(12) United States Patent
Hemmati et al.

(10) Patent No.: US 10,695,293 B2
(45) Date of Patent: Jun. 30, 2020

(54) METHOD OF PREVENTING OR TREATING RADIATION-INDUCED DERMATITIS WITH EXTRACELLULAR VESICLES

(71) Applicant: Capricor, Inc., Beverly Hills, CA (US)

(72) Inventors: Houman Hemmati, Los Angeles, CA (US); Luis Rodriguez-Borlado, Manhattan Beach, CA (US); Kiel A. Peck, West Hollywood, CA (US); Linda Marban, Santa Monica, CA (US)

(73) Assignee: Capricor, Inc., Beverly Hills, CA (US)

( * ) Notice: Subject to any disclaimer, the term of this patent is extended or adjusted under 35 U.S.C. 154(b) by 0 days.

(21) Appl. No.: 16/086,736

(22) PCT Filed: Mar. 17, 2017

(86) PCT No.: PCT/US2017/023066
§ 371 (c)(1),
(2) Date: Sep. 20, 2018

(87) PCT Pub. No.: WO2017/165235
PCT Pub. Date: Sep. 28, 2017

(65) Prior Publication Data
US 2019/0099370 A1  Apr. 4, 2019

Related U.S. Application Data

(60) Provisional application No. 62/311,905, filed on Mar. 22, 2016.

(51) Int. Cl.
| | |
|---|---|
| *A61K 9/127* | (2006.01) |
| *A61K 9/00* | (2006.01) |
| *A61K 35/28* | (2015.01) |
| *A61K 35/34* | (2015.01) |
| *A61K 47/10* | (2017.01) |
| *A61P 17/02* | (2006.01) |

(52) U.S. Cl.
CPC ............ *A61K 9/127* (2013.01); *A61K 9/0014* (2013.01); *A61K 9/0019* (2013.01); *A61K 35/28* (2013.01); *A61K 35/34* (2013.01); *A61K 47/10* (2013.01); *A61P 17/02* (2018.01)

(58) Field of Classification Search
CPC ...... A61K 9/0014; A61K 9/127; A61K 35/34; A61K 47/10; A61K 35/28; A61K 9/0019; A61P 17/02
See application file for complete search history.

(56) References Cited

U.S. PATENT DOCUMENTS

2006/0222622 A1* 10/2006 Faure .................. A61K 8/64
424/78.27
2015/0024011 A1* 1/2015 Lim ..................... A61K 8/14
424/400

OTHER PUBLICATIONS

Zhang et al. Exosomes released from human induced pluripotent stem cells-derived MSCs facilitate cutaneous wound healing by promoting collagen synthesis and angiogenesis. Journal of Translational Medicine (Feb. 2015), 13(49), 14 pages. (Year: 2015).*
Barile et al. Ultrastructural Evidence of Exosome Secretion by Progenitor Cells in Adult Mouse Myocardium and Adult Human Cardiospheres. Journal of Biomedicine and Biotechnology (2012), article ID 354605, 10 pages. (Year: 2015).*
Ibrahim et al. Exosomes as Critical Agents of Cardiac Regeneration Triggered by Cell Therapy. Stem Cell Reports (2014), v2, 606-619. (Year: 2014).*

* cited by examiner

*Primary Examiner* — Sean C. Barron
(74) *Attorney, Agent, or Firm* — Tony K. Uhm

(57) ABSTRACT

The present invention relates to a method of treating dermatitis, in particular radiation-induced dermatitis, with extracellular vesicles, in particular exosomes obtained from human cardiospheres or cardiosphere-derived cells. The present invention also provides a formulation comprising extracellular vesicles, in particular exosomes obtained from human cardiospheres or cardiosphere-derived cells, for use in the treatment of dermatitis, in particular radiation-induced dermatitis.

19 Claims, 12 Drawing Sheets

Arrows indicate day of radiation exposure, or dosing of test article/vehicle. * = p < 0.05.

Arrows indicate days of radiation exposure, or dosing of test article/vehicle. * = p < 0.05;  = p < 0.01; * = p < 0.001

* = p < 0.05;  = p < 0.01; * = p < 0.001

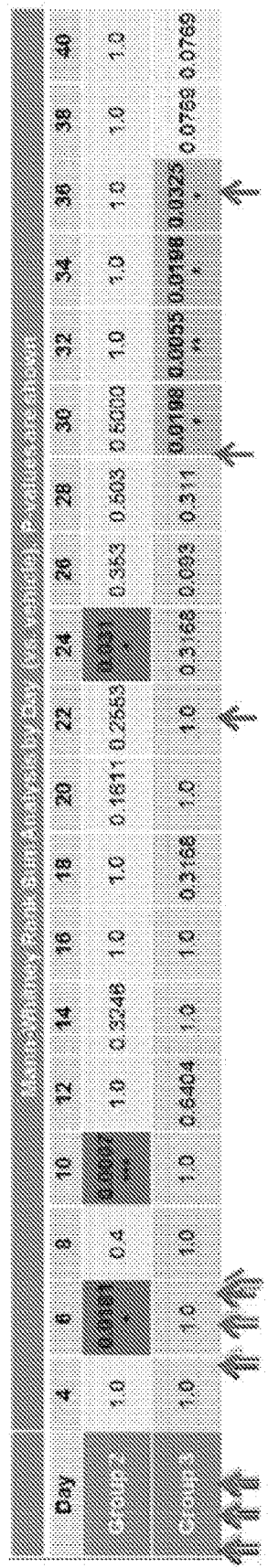

Fig. 9

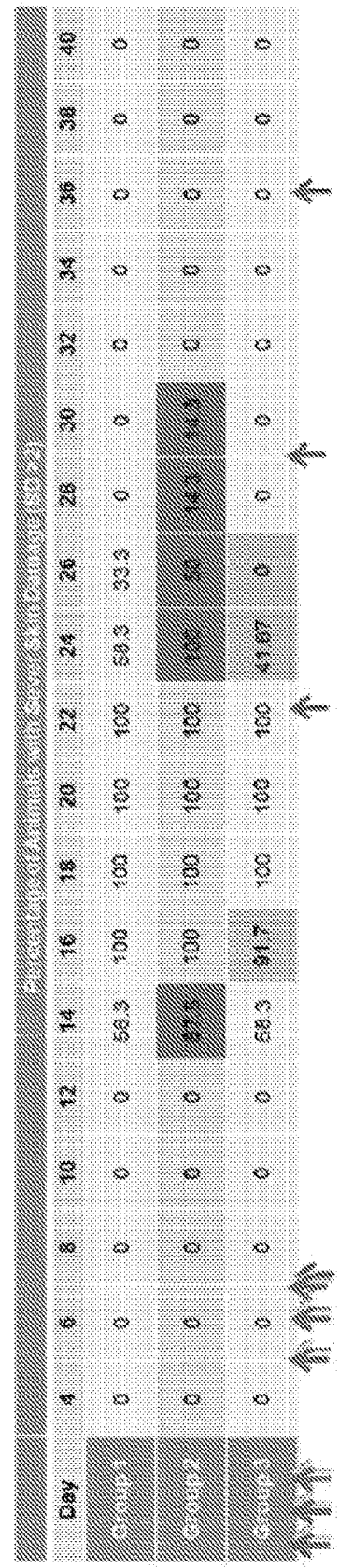

Fig. 10

Green shading indicates improvement, red shading indicates exacerbation of damage compared to the vehicle control on the indicated day. Bold font denotes significant difference in skin damage scores. Red arrows indicated radiation exposures (10 Gy each). Light blue arrows indicate dosing with low-dose (0.25 mg/mL; Group 2) CDC-EVs. Dark blue arrows indicate dosing with high-dose (1.5 mg/mL) CDC-EVs. $* = p < 0.05$; $ = p < 0.01$; $* = p < 0.001$.

Green denotes decrease in comparison to the vehicle group; red denotes increase.

Arrows indicate day of radiation exposure, or dosing of the test article/vehicle control.

\* = p < 0.05; \*\* = p < 0.01; \*\*\* = p < 001

\* = p < 0.05; \*\* = p < 0.01; \*\*\* = p < 001

\* = p < 0.05

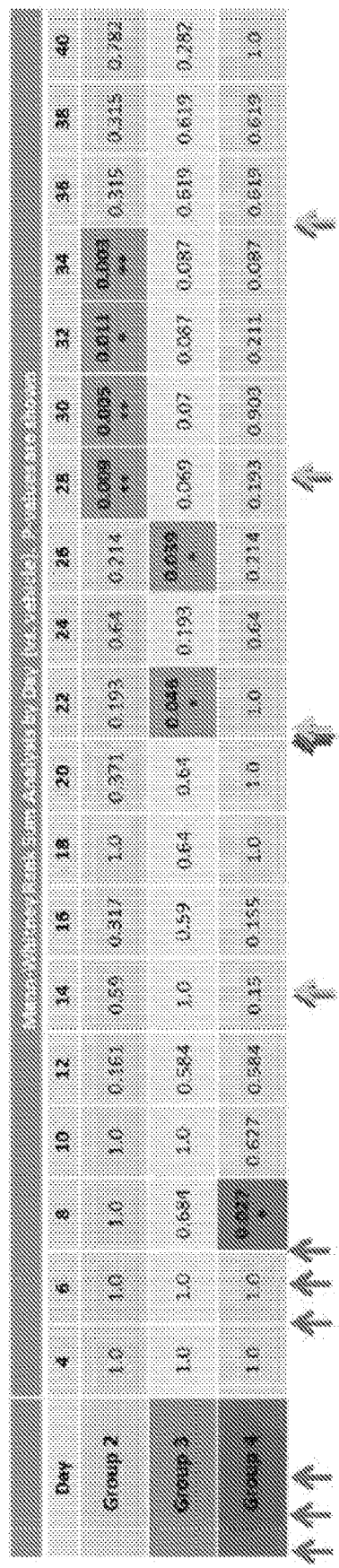

Fig. 16

Green shading indicates improvement, red shading indicates exacerbation of damage compared to vehicle control on the indicated day. Bold font denotes statistical significant difference in skin damage scores. Red arrows indicated radiation exposures (10 Gy each). Light blue arrows indicate dosing with low-dose (0.25 mg/mL) CDC-EVs; Group 2) CDC-EVs. Dark blue arrows indicate dosing with high-dose (1.5 mg/mL; Group 3) CDC-EVs. Purple arrow indicates single dosing of high-dose (1.5 mg/mL) CDC-EVs. * = p < 0.05, ** = p < 0.01.

* = p < 0.05

METHOD OF PREVENTING OR TREATING RADIATION-INDUCED DERMATITIS WITH EXTRACELLULAR VESICLES

BACKGROUND OF THE INVENTION

Radiation therapy is a powerful tool for the treatment of a wide range of cancers. Since radiation must penetrate the skin to reach the tumor site, the skin receives dose-dependent damage during radiation treatment. The skin is susceptible to radiation damage, because it is a continuously renewing organ, which contains rapidly proliferating and maturing cells, with basal keratinocytes, hair follicle stem cells and melanocytes being very radiosensitive. See, e.g., Ryan, *Ionizing radiation: the good, the bad, and the ugly*, J Invest Dermatol, 132:985-93 (2012). The most sensitive skin areas are the anterior of the neck, extremities, chest, abdomen and face, along with the hair follicles on the scalp and breast tissue. See, e.g., McQuestion, *Evidence-based skin care management in radiation therapy: clinical update*, Semin Oncol Nurs, 27:e1-17 (2011). The skin injury manifests itself as radiation-induced dermatitis in approximately 95% of patients receiving radiotherapy, with the injury ranging from mild erythema to moist desquamation and skin ulceration. See, e.g., Brown et al., *Acute and chronic radiation injury*, J Vasc Surg, 53:15S (2011). Approximately 20-25% of patients receiving radiotherapy experience moist desquamation and ulceration. See, e.g., *Consensus guidelines for the management of radiation dermatitis and coexisting acne-like rash in patients receiving radiotherapy plus EGFR inhibitors for the treatment of squamous cell carcinoma of the head and neck*, Ann Oncol, 19:142 (2008). Radiation dermatitis has a profound impact on the quality of a patient's life, due to pain, itching, and poor aesthetic appearance. In addition it may be the cause of premature interruption of radiation therapy, resulting in inadequate disease treatment. See, e.g., Isomura et al., *IL12RB2 and ABCA1 genes are associated with susceptibility to radiation dermatitis*, Clin Cancer Res, 14:6683 (2008). In the long term, skin wounds can reappear due to abnormal pathological changes, such as excessive fibrosis that can occur during the initial phases of the healing process. See, e.g., Olascoaga et al., *Wound healing in radiated skin: pathophysiology and treatment options*, Int Would J, 5:246-57 (2008).

Radiation-induced dermatitis is primarily due to cellular oxidative stress by generation of reactive oxygen species (ROS) such as peroxides and superoxide, as well as the highly reactive hydroxyl and hydrogen radicals. See, e.g., Niwa et al., *Protein oxidation damage in the stratum corneum: Evidence for a link between environmental oxidants and the changing prevalence and nature of atopic dermatitis in Japan*, Br J Dermatol, 149:248-254 (2003). Furthermore, proinflammatory processes such as cytokine release and inflammatory cell infiltration lead to further ROS generation, damage and disease pathology. Rosenthal et al., *Salen Mn complexes mitigate radiation injury in normal tissues*, Anticancer Agents Med Chem, 11:359-72 (2011).

The most common strategy for preventing and minimizing radiation-induced dermatitis involves simple moisturization of the irradiated area and using a mild soap to keep the area clean. See, e.g., Maddocks-Jennings et al., *Novel approaches to radiotherapy-induced skin reactions: a literature review*, Complement Ther Clin Pract, 11:224-31 (2005). However, all of the currently used treatment regimens lack clinically significant efficacy. For example, the use of aloe vera gel, hyaluronidase-based creams or sucralfate creams, did not result in significant improvements in dermatitis scoring. See, e.g., Salvo et al., *Prophylaxis and management of acute radiation-induced skin reactions: a systematic review of the literature*, Curr Oncol, 17:94-112 (2010). As such, there remains a need for an effective pharmacologic treatment for dermatitis, in particular radiation-induced dermatitis.

Cells release into the extracellular environment diverse types of membrane vesicles of endosomal and plasma membrane origin called exosomes and microvesicles, respectively. These extracellular vesicles represent an important mode of intercellular communication by serving as vehicles for transfer between cells of membrane and cytosolic proteins, lipids, and RNA. See, e.g., Graça Raposo and Willem Stoorvogel, *Extracellular Vesicles: Exosomes, Microvesicles, and Friends*, The Journal of Cell Biology, Vol. 200, No. 4, 373-383 (2013). WO 2014/028493 describes exosomes derived cardiosphere-derived cells (CDCs) and their therapeutic utility for the repair or regeneration of damaged or diseased cells or tissue, e.g., damaged cardiac tissue. US 2012/0315252 in turn describes CDCs, their derivation from cardiospheres, and their therapeutic utility for increasing the function of a damaged or diseased heart of a mammal. WO 2005/012510 in turn describes cardiospheres, their derivation from human or animal cardiac tissue biopsy samples, and their therapeutic utility in cell transplantation and functional repair of the myocardium or other organs.

SUMMARY OF THE INVENTION

The present invention is based on the surprising discovery by the present inventors that extracellular vesicles, e.g., exosomes, would be effective in treating dermatitis, in particular radiation-induced dermatitis. Since there was no recognition whatsoever in the art as to the potential therapeutic utility of extracellular vesicles, e.g., exosomes, to treat radiation-induced dermatitis, the present invention is based on the surprising finding by the present inventors that certain extracellular vesicles, e.g., exosomes derived from certain cell populations, e.g., cardiosphere-derived cells (CDCs), were shown to be efficacious in treating a subject with radiation-induced dermatitis, as confirmed in relevant animal model experiments as described herein.

A first aspect of the present invention provides a method of preventing or treating cutaneous injury, in particular dermatitis, and further in particular radiation-induced acute or chronic dermatitis, in a subject in need thereof, the method comprising administrating to the subject a therapeutically effective amount of extracellular vesicles.

A second aspect of the present invention provides a formulation comprising extracellular vesicles for use in the prevention or treatment of cutaneous injury, in particular dermatitis, and further in particular acute or chronic radiation-induced dermatitis, e.g., fractionated radiation.

In some embodiments, the extracellular vesicle is an exosome, microvesicle, membrane particle, membrane vesicle, exosome-like vesicle, ectosome, ectosome-like vesicle, exovesicle, epididimosome, argosome, promininosome, prostasome, dexosome, texosome, archeosome, oncosome, or the like.

In several embodiments, the subject is a mammal, preferably a human, and more preferably a human patient who has undergone, is undergoing, or is about to undergo, radiation therapy, e.g., cancer radiotherapy.

In some embodiments, a therapeutically effective amount of extracellular vesicles, e.g., exosomes, is administered to a subject after the subject has received one or more doses of radiation. In some embodiments, a therapeutically effective amount of extracellular vesicles, e.g., exosomes, is administered to a subject less than, e.g., 1 hour post each radiation exposure. In some embodiments, a therapeutically effective amount of extracellular vesicles, e.g., exosomes, is administered to a subject less than, e.g., 1-24 hours post radiation exposure. In some embodiments, a therapeutically effective amount of extracellular vesicles, e.g., exosomes, is administered to a subject less than, e.g., 24-48 hours post radiation exposure. In some embodiments, a therapeutically effective amount of extracellular vesicles, e.g., exosomes, is administered to a subject after one or more of the acute or chronic clinical manifestations of radiation-induced dermatitis have occurred. In some embodiments, a therapeutically effective amount of extracellular vesicles, e.g., exosomes, is administered to a subject, e.g., 10-14 days after the subject has received one or more doses of radiation. In some embodiments, a therapeutically effective amount of extracellular vesicles, e.g., exosomes, is administered to a subject, e.g., 15-21 days after an initial radiation exposure. In some embodiments, a therapeutically effective amount of extracellular vesicles, e.g., exosomes, is administered to a subject, e.g., 1-2 weeks after an initial radiation exposure. In some embodiments, a therapeutically effective amount of extracellular vesicles, e.g., exosomes, is administered to a subject, e.g., 2-3 weeks after an initial radiation exposure. In some embodiments, a therapeutically effective amount of extracellular vesicles, e.g., exosomes, is administered to a subject, e.g., 4-8 weeks after an initial radiation exposure. In some embodiments, a therapeutically effective amount of extracellular vesicles, e.g., exosomes, is administered to a subject, e.g., 1, 2, 3, 4, 5, 6, 7, and/or 8 weeks after an initial radiation exposure, one or more times, e.g., 7 days apart between successive administrations.

In some embodiments, a therapeutically effective amount of extracellular vesicles, e.g., exosomes, is administered to a subject, e.g., 1-2 weeks after a final dose of radiation has been administered. In some embodiments, a therapeutically effective amount of extracellular vesicles, e.g., exosomes, is administered to a subject, e.g., 2-3 weeks after a final dose of radiation has been administered. In some embodiments, a therapeutically effective amount of extracellular vesicles, e.g., exosomes, is administered to a subject, e.g., 4-5 weeks after a final dose of radiation has been administered. In some embodiments, a therapeutically effective amount of extracellular vesicles, e.g., exosomes, is administered to a subject, e.g., 6-7 weeks after a final dose of radiation has been administered. In some embodiments, a therapeutically effective amount of extracellular vesicles, e.g., exosomes, is administered to a subject, e.g., 1, 2, 3, 4, 5, 6, 7, and/or 8 weeks after a final dose of radiation has been administered, one or more times, e.g., 7 days apart between successive administrations.

In some embodiments, a therapeutically effective amount of extracellular vesicles, e.g., exosomes, is administered to a subject after the subject has developed generalized erythema caused by radiation.

In several embodiments, dermatitis is caused by radiation therapy, in particular radiotherapy for the treatment of a wide range of cancers such as head and neck cancer, breast cancer, sarcoma, pediatric sarcoma, mycosis fungoides, melanoma, lung cancer, Sézary syndrome, and the like. In additional embodiments, the dermatitis is induced by radiotherapy for the treatment of ovarian cancer, pancreatic cancer, colorectal carcinoma, prostate cancer, melanoma, liver cancer, brain tumors, multiple myeloma, leukemia, cervical cancer, gastric cancer, renal cell carcinoma, hepatocellular carcinomas, lymphomas, and the like. In additional embodiments, dermatitis is caused by exposure to radiation due to accident or hostile activity, exposure to ultraviolet (UV) radiation, or the like. In additional embodiments, dermatitis is caused by electron therapy or electron beam therapy (EBT), such as total skin electron therapy (TSET) for the treatment of, e.g., cutaneous T cell lymphoma such as mycosis fungoides and Sézary syndrome.

In several embodiments, said administration is via subcutaneous injection, transcutaneous injection, intradermal injection, topical administration, intramuscular injection, injection into lymphoid tissue, injection into the lymphatic system, systemic administration (e.g., oral, intravenous, intraparenteral), or the like.

In several embodiments, extracellular vesicles, e.g., exosomes, are formulated in a crystalloid solution (e.g., Plasmalyte, normal saline), aqueous solution, gel, ointment, cream, topical or implantable hydrogel, powder, spray, sustained-release polymer (e.g., PLGA and PLA), polyethylene glycol (PEG)-containing solution, suspension, emulsion, as part of a drug delivery device, insert, patch, or the like. In several embodiments, prior to use, extracellular vesicles, e.g., exosomes, are resuspended in an appropriate buffer, e.g., sterile PBS with or without human serum albumin. In some embodiments, exosomes can be stored for future use, e.g., frozen at −80° C.

In several embodiments, extracellular vesicles, e.g., exosomes, are derived from human or animal cells. In several embodiments, extracellular vesicles, e.g., exosomes, are prepared from cardiospheres or CDCs, or from newt A1 cell line. In some embodiments, extracellular vesicles, e.g., exosomes, are prepared from regenerative stem cells such as embryonic stem cells, pluripotent stem cells, multipotent stem cells, induced pluripotent stem cells, post-natal stem cells, adult stem cells, mesenchymal stem cells, hematopoietic stem cells, endothelial stem cells, epithelial stem cells, neural stem cells, cardiac stem cells including cardiac progenitor cells, bone marrow-derived stem cells, adipose-derived stem cells, hepatic stem cells, peripheral blood derived stem cells, cord blood-derived stem cells, placental stem cells, or the like.

In several embodiments, extracellular vesicles, e.g., exosomes, are modified (e.g., genetically or otherwise) to direct them to a specific target site. For example, a modification may, in some embodiments, comprise inducing expression of a specific cell-surface marker on the exosome, which results in specific interaction with a receptor on a desired target tissue. In one embodiment, the native contents of the exosome are removed and replaced with, or supplemented with, desired exogenous proteins and/or nucleic acids.

In several embodiments, extracellular vesicles, e.g., exosomes, include one or more microRNAs selected from: miR-146a, miR-148a, miR-22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a. In a preferred embodiment, extracellular vesicles, e.g., exosomes, comprise miR-146a and miR-210. In several embodiments, extracellular vesicles, e.g., exosomes, include one or more microRNAs selected from: hsa-miR-23a-3p, hsa-miR-130a-3p, hsa-miR-21-5p, hsa-miR-4516, hsa-let-7a-5p, hsa-miR-125b-5p, hsa-miR-199a-3p, hsa-miR-199b-3p, hsa-miR-22-3p, hsa-miR-24-3p, hsa-miR-1290, hsa-miR-320e, hsa-miR-423-5p, hsa-miR-22-3p, hsa-miR-222-3p (also known as miR-221-3p), hsa-miR-100-5p, hsa-miR-337-5p, hsa-miR-27b-3p, hsa-miR-1915-3p, and hsa-miR-29b-3p, hsa-miR-25-3p (also known as miR-92a-3p).

In several embodiments, extracellular vesicles, e.g., exosomes, contain biological proteins, e.g., transcription factors, cytokines, growth factors, and similar proteins capable of modulating signaling pathways in a target cell. In some embodiments, the biological protein is capable of facilitating regeneration and/or improved function of a tissue. In some embodiments, the biological protein is capable of modulating pathways related to Irak1, Traf6, toll-like receptor (TLR) signaling pathway, NOX-4, SMAD-4, and/or TGF-β. In some embodiments, the biological protein is related to exosome formation and packaging of cytosolic proteins such as Hsp70, Hsp90, 14-3-3 epsilon, PKM2, GW182 and AGO2. In some embodiments, extracellular vesicles, e.g., exosomes, contain signaling lipids, e.g., ceramide and derivatives.

In several embodiments, extracellular vesicles, e.g., exosomes, express tetraspanins, e.g., CD63, CD81, CD82, CD53, and/or CD37. In some embodiments, extracellular vesicles, e.g., exosomes, express one or more lipid raft associated proteins (e.g., glycosylphosphatidylinositol-anchored proteins and flotillin), cholesterol, sphingomyelin, and/or hexosylceramides.

In several embodiments, extracellular vesicles, e.g., exosomes, have a diameter of, e.g., about 15-250 nm, about 15-205 nm, about 90-220 nm, about 30-200 nm, about 20-150 nm, about 70-150 nm, or about 40-100 nm. In several embodiments, extracellular vesicles, e.g., microvesicles, have a diameter of, e.g., about 100-1000 nm.

In several embodiments, extracellular vesicles, e.g., exosomes, are purified such that contaminants or undesired compounds are removed from the exosomes. In some embodiments, the patient is administered substantially purified exosomes such that about 50% to 90%, or up to 100%, of the contaminants are removed from the exosomes. In some embodiments, an exosome preparation is essentially free of non-exosome components.

In several embodiments, extracellular vesicles, e.g., exosomes, are administered in combination with one or more additional agents. For example, in several embodiments, the exosomes are administered in combination with one or more proteins or nucleic acids derived from the exosome. In several embodiments, the cells from which the exosomes are isolated are administered in conjunction with the exosomes. In several embodiments, such an approach advantageously provides an acute and more prolonged duration of exosome delivery (e.g., acute based on the actual exosome delivery and prolonged based on the cellular delivery, the cells continuing to secrete exosomes post-delivery).

In several embodiments, the dose of extracellular vesicles, e.g., exosomes ranges about $1.0 \times 10^5$ to about $1.0 \times 10^9$ exosomes. In certain embodiments, the exosome dose is administered on a per kilogram basis, e.g., about $1.0 \times 10^5$ exosomes/kg to about $1.0 \times 10^9$ exosomes/kg. In additional embodiments, exosomes are delivered in an amount based on the mass of the target tissue, e.g., about $1.0 \times 10^5$ exosomes/gram of target tissue to about $1.0 \times 10^9$ exosomes/gram of target tissue. In several embodiments, exosomes are administered based on a ratio of the number of exosomes the number of cells in a particular target tissue. If exosomes are to be administered in conjunction with the concurrent therapy (e.g., cells that can still shed exosomes, pharmaceutical therapy, nucleic acid therapy, and the like) the dose of exosomes administered can be adjusted accordingly (e.g., increased or decreased as needed to achieve the desired therapeutic effect).

BRIEF DESCRIPTION OF THE DRAWINGS

FIG. 9 shows comparison of daily dermatitis scores, for $1^{st}$ Experiment.

FIG. 10 shows % of the experimental animals with severe skin damages by day, for $1^{st}$ Experiment.

FIG. 16 shows comparison of daily dermatitis scores, for $2^{nd}$ Experiment.

DETAILED DESCRIPTION OF THE INVENTION

A) Clinical Manifestations

Figure 1:
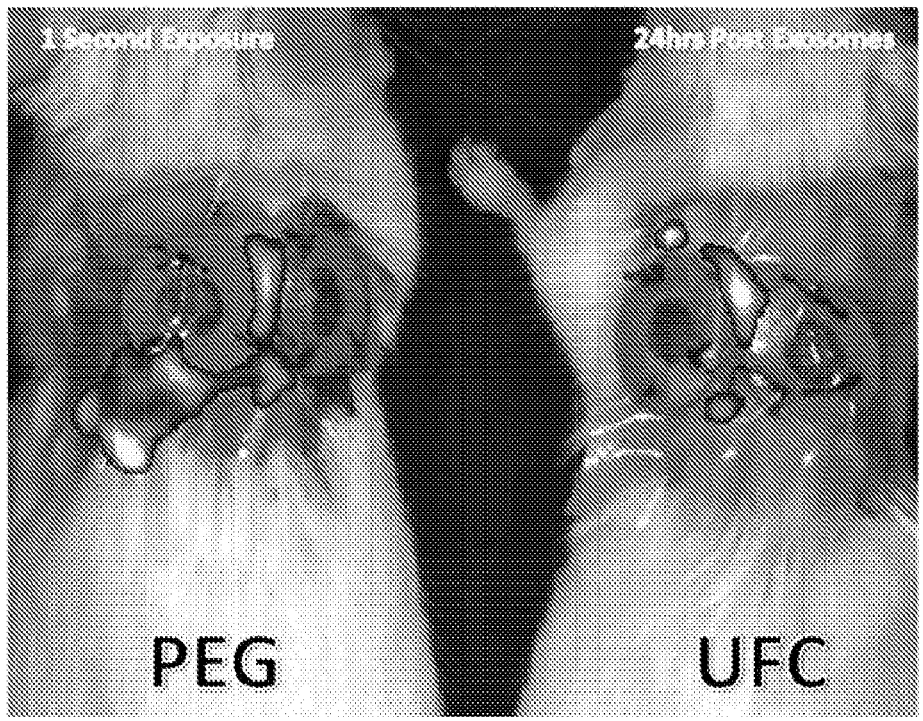
FIG. 1 shows biodistribution of DiR labelled exosomes 24 hours after subcutaneous injection into the back of mice.

Acute radiation-induced skin changes usually occur within 90 days, depend upon the radiation dose, and include erythema, edema, pigment changes, epilation, and dry or moist desquamation. See, e.g., Jensen et al., "Treatment of acute radiodermatitis with an oil-in-water emulsion following radiation therapy for breast cancer: a controlled, randomized trial," *Strahlenther Onkol*, 187:378 (2011). Generalized erythema may occur hours after radiation exposure, is normally only evident with doses of 2 gray (Gy) or higher, and fades within hours to days. See, e.g., "Schmuth et al., "Permeability barrier function of skin exposed to ionizing radiation," *Arch Dermatol*, 137:1019-23 (2001). A second phase of more sustained erythema is apparent 10-14 days after dosing. Dry desquamation occurs at doses of 12-20 Gy, moist desquamation at ≥20 Gy, and necrosis at >35 or higher. See, e.g., Mendelsohn et al., "Wound care after radiation therapy,"*Adv Skin Wound Care*, 15(5):216 (2002). Table 1 shows the classification of radiation-induced dermatitis according to the National Cancer Institute's Common Toxicity Criteria for Adverse Events (CTCAE), version 4.03 (Jun. 14, 2010), wherein radiation dermatitis is defined as "[a] finding of cutaneous inflammatory reaction occurring as a result of exposure to biologically effective levels of ionizing radiation."

TABLE 1

| Grade | | | |
|---|---|---|---|
| 1 | 2 | 3 | 4 |
| Faint erythema or dry desquamation | Moderate to brisk erythema; patchy moist desquamation, mostly confined to skin folds and creases; moderate edema | Moist desquamation in areas other than skin folds and creases; bleeding induced by minor trauma or abrasion | Life-threatening consequences; skin necrosis or ulceration of full thickness dermis; spontaneous bleeding from involved site; skin graft indicated |

Chronic radiation dermatitis may not develop for months to years after radiation exposure. It is characterized by dermal fibrosis, and poikilodermatous skin changes, including dyspigmentation, atrophy, and telangiectasia. See, e.g., Brown and Rzucidlo, "Acute and chronic radiation injury," *J Vasc Surg,* 53:15S (2011). Fibrosis in response to growth factors, such as transforming growth factor-β(TGF-β), may be focal or widespread, producing tissue retraction, limitation of movement, and pain. See, e.g., Canney and Dean, "Transforming growth factor beta: a promoter of late connective tissue injury following radiotherapy?," *Br J Radiol,* 63:620-3 (1990). Eccentric myointimal proliferation of the small arteries and arterioles may progress to thrombosis or obstruction, increasing the predisposition for ulcers and skin breakdown. Mendelsohn et al., "Wound care after radiation therapy,"*Adv Skin Wound Care,* 15:216-24 (2002). Skin atrophy, related to decreased population of dermal fibroblasts and the reabsorption of collagen also causes fragility and predisposes to erosions and ulcerations. See, e.g., Harper et al., "Skin toxicity during breast irradiation: pathophysiology and management," *South Med J,* 97:989-93 (2004). Radiation necrosis is more commonly a late-consequential injury associated with high-dose radiotherapy, failure to heal, acute dermatitis, and dermal ischemia. See, e.g., Hopewell, "The skin: its structure and response to ionizing radiation," *Int J Radiat Biol,* 57:751-73 (1990).

For the purpose of the present invention, the term "dermatitis" comprises cutaneous inflammation, as well as consequential cutaneous injuries associated therewith.

B) Cardiospheres

Cardiospheres are undifferentiated cardiac cells that grow as self-adherent clusters as described in WO 2005/012510, and Messina et al., "Isolation and Expansion of Adult Cardiac Stem Cells From Human and Murine Heart," *Circulation Research,* 95:911-921 (2004), the disclosures of which are herein incorporated by reference in their entirety.

Briefly, heart tissue can be collected from a patient during surgery or cardiac biopsy. The heart tissue can be harvested from the left ventricle, right ventricle, septum, left atrium, right atrium, crista terminalis, right ventricular endocardium, septal or ventricle wall, atrial appendages, or combinations thereof. A biopsy can be obtained, e.g., by using a percutaneous bioptome as described in, e.g., U.S. Patent Application Publication Nos. 2009/012422 and 2012/0039857, the disclosures of which are herein incorporated by reference in their entirety. The tissue can then be cultured directly, or alternatively, the heart tissue can be frozen, thawed, and then cultured. The tissue can be digested with protease enzymes such as collagenase, trypsin and the like. The heart tissue can be cultured as an explant such that cells including fibroblast-like cells and cardiosphere-forming cells grow out from the explant. In some instances, an explant is cultured on a culture vessel coated with one or more components of the extracellular matrix (e.g., fibronectin, laminin, collagen, elastin, or other extracellular matrix proteins). The tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy. Cells surrounding the explant including cardiosphere-forming cells can be collected by manual methods or by enzymatic digestion. The collected cardiosphere-forming cells can be cultured under conditions to promote the formation of cardiospheres. In some aspects, the cells are cultured in cardiosphere-growth medium comprising buffered media, amino acids, nutrients, serum or serum replacement, growth factors including but not limited to EGF and bFGF, cytokines including but not limited to cardiotrophin, and other cardiosphere promoting factors such as but not limited to thrombin. Cardiosphere-forming cells can be plated at an appropriate density necessary for cardiosphere formation, such as about 20,000-100,000 cells/mL. The cells can be cultured on sterile dishes coated with poly-D-lysine, or other natural or synthetic molecules that hinder the cells from attaching to the surface of the dish. Cardiospheres can appear spontaneously about 2-7 days or more after cardiosphere-forming cells are plated.

C) Cardiosphere-Derived Cells (CDCs)

CDCs are a population of cells generated by manipulating cardiospheres in the manner as described in, e.g., U.S. Patent Application Publication No. 2012/0315252, the disclosures of which are herein incorporated by reference in their entirety. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, gelatin, or poly-D-lysine, and expanding same as an adherent monolayer culture. CDCs can be repeatedly passaged, e.g., passaged two times or more, according to standard cell culturing methods.

D) Exosomes

Exosomes are vesicles formed via a specific intracellular pathway involving multivesicular bodies or endosomal-related regions of the plasma membrane of a cell. Exosomes can range in size from approximately 20-150 nm in diameter. In some cases, they have a characteristic buoyant density of approximately 1.1-1.2 g/mL, and a characteristic lipid composition. Their lipid membrane is typically rich in cholesterol and contains sphingomyelin, ceramide, lipid rafts and exposed phosphatidylserine. Exosomes express certain marker proteins, such as integrins and cell adhesion molecules, but generally lack markers of lysosomes, mitochondria, or caveolae. In some embodiments, the exosomes contain cell-derived components, such as but not limited to, proteins, DNA and RNA (e.g., microRNA and noncoding RNA). In some embodiments, exosomes can be obtained from cells obtained from a source that is allogeneic, autologous, xenogeneic, or syngeneic with respect to the recipient of the exosomes.

Certain types of RNA, e.g., microRNA (miRNA), are known to be carried by exosomes. miRNAs function as post-transcriptional regulators, often through binding to complementary sequences on target messenger RNA transcripts (mRNAs), thereby resulting in translational repression, target mRNA degradation and/or gene silencing. For example, as described in WO 2014/028493, miR146a exhibits over a 250-fold increased expression in CDCs, and miR210 is upregulated approximately 30-fold, as compared to the exosomes isolated from normal human dermal fibroblasts.

Exosomes derived from cardiospheres and CDCs are described in, e.g., WO 2014/028493, the disclosures of which are herein incorporated by reference in their entirety. Methods for preparing exosomes can include the steps of: culturing cardiospheres or CDCs in conditioned media, isolating the cells from the conditioned media, purifying the exosome by, e.g., sequential centrifugation, and optionally, clarifying the exosomes on a density gradient, e.g., sucrose density gradient. In some instances, the isolated and purified exosomes are essentially free of non-exosome components, such as components of cardiospheres or CDCs. Exosomes can be resuspended in a buffer such as a sterile PBS buffer containing 0.01-1% human serum albumin. The exosomes may be frozen and stored for future use.

Exosomes can be prepared using a commercial kit such as, but not limited to the ExoSpin™ Exosome Purification Kit, Invitrogen® Total Exosome Purification Kit, PureExo® Exosome Isolation Kit, and ExoCap™ Exosome Isolation kit. Methods for isolating exosome from stem cells are found in, e.g., Tan et al., Journal of Extracellular Vesicles, 2:22614 (2013); Ono et al., Sci Signal, 7(332):ra63 (2014) and U.S. Application Publication Nos. 2012/0093885 and 2014/0004601. Methods for isolating exosome from cardiosphere-derived cells are found in, e.g., Ibrahim et al., Stem Cell Reports, 2:606-619 (2014). Collected exosomes can be concentrated and/or purified using methods known in the art. Specific methodologies include ultracentrifugation, density gradient, HPLC, adherence to substrate based on affinity, or filtration based on size exclusion.

For example, differential ultracentrifugation has become a leading technique wherein secreted exosomes are isolated from the supernatants of cultured cells. This approach allows for separation of exosomes from nonmembranous particles, by exploiting their relatively low buoyant density. Size exclusion allows for their separation from biochemically similar, but biophysically different microvesicles, which possess larger diameters of up to 1,000 nm. Differences in flotation velocity further allows for separation of differentially sized exosomes. In general, exosome sizes will possess a diameter ranging from 30-200 nm, including sizes of 40-100 nm. Further purification may rely on specific properties of the particular exosomes of interest. This includes, e.g., use of immunoadsorption with a protein of interest to select specific vesicles with exoplasmic or outward orientations.

Among current methods, e.g., differential centrifugation, discontinuous density gradients, immunoaffinity, ultrafiltration and high performance liquid chromatography (HPLC), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/mL) or application of a discrete sugar cushion in preparation.

Importantly, ultrafiltration can be used to purify exosomes without compromising their biological activity. Membranes with different pore sizes—such as 100 kDa molecular weight cut-off (MWCO) and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. HPLC can also be used to purify exosomes to homogeneouslysized particles and preserve their biological activity as the preparation is maintained at a physiological pH and salt concentration.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolate specific exosomes of interest. This includes relying on antibody immunoaffinity to recognizing certain exosome-associated antigens. As described, exosomes further express the extracellular domain of membrane-bound receptors at the surface of the membrane. This presents a ripe opportunity for isolating and segregating exosomes in connections with their parental cellular origin, based on a shared antigenic profile. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

E) Examples

The present invention is further described with reference to the following non-limiting examples.

Example 1: CDC Culture

CDCs were prepared as described in U.S. Patent Application Publication No. 2012/0315252, the disclosures of which are herein incorporated by reference in their entirety. In brief, heart biopsies were minced into small fragments and briefly digested with collagenase. Explants were then cultured on 20 mg/mL fibronectin-coated dishes. Stromal-like flat cells and phase-bright round cells grew out spontaneously from tissue fragments and reached confluency by 2-3 weeks. These cells were harvested using 0.25% trypsin and were cultured in suspension on 20 mg/mL poly-d-lysine to form self-aggregating cardiospheres. CDCs were obtained by plating and expanding the cardiospheres on a fibronectin-coated flask as an adherent monolayer culture. All cultures were maintained at 5% $O_2$, 5% $CO_2$ at 37° C., using IMDM basic medium supplemented with 10% FBS, 1% penicillin/streptomycin, and 0.1 mL 2-mercaptoethanol. CDCs were grown to 100% confluency on a fibronectin-coated flask to passage 5.

Example 2: Isolation of Exosomes from CDCs

When the CDCs reached the desired confluency, the flask was washed three times with PBS. CDCs were treated with serum-free medium (IMDM) and were incubated at 37° C. at 5% $O_2$, 5% $CO_2$ for 15 days. After 15 days, the conditioned medium was collected in 225 mL BD Falcon polypropylene conical tubes (BD 352075—Blue Top) and centrifuged at 2,000 rpm for 20 minutes at 4° C. to remove cells and debris (care was taken not to disturb the pellet). The conditioned medium was run through a 0.45 µm membrane filter. The conditioned medium was concentrated using centrifugal filter. A 3 KDa Centricon Plus-70 Centrifugal Filter was pre-rinsed with 10-25 mL of molecular grade water and was centrifuged at 3220 g for five minutes at 18° C. Once the filter was rinsed, all remaining water was carefully removed without touching the filter. 15 mL of the conditioned medium was added to the filter and was centrifuged at 3220 g for 45 minutes at 18° C. After the initial spin, the remaining medium was mixed by pipetting and then spun again until the desired concentration was reached. The final sample was then run through a 0.22 µm syringe filter. 25 µL of the concentrated conditioned medium was diluted in 975 µL of PBS for particle count using the Nanosight. Another 100 µL of the concentrated conditioned medium was used to measure protein concentration. Protein was quantified using the DC protein Assay. In some cases, historical data was used to calculate the concentration of protein in the ultra-filtration by centrifugation (UFC) sample. The concentrated conditioned medium was used immediately or was stored at −80° C.

Example 3: Exosome Precipitation with 25% Polyethylene Glycol (PEG)

The appropriate volume of 25% PEG was added to the filtered concentrated conditioned medium. The samples were incuated at 4° C. for 12-16 hours on an orbital shaker. Once incubation was complete, the samples were centrifuged at 1500 g for 30 minutes at 4° C. The supernatant was carefully removed without disrupting the pellet. The pellet was resuspended in the desired volume of serum-free medium and sampled for particle count.

Example 3A: CDC-EVs (10 KDa Method & 1000 KDa Method); MSC-EVs; Newt-EVs

A) 10 KDa & 1000 KDa

CDC-EV (10 KDa or 1000 KDa) drug substance is obtained after filtering CDC conditioned medium (CM) containing EVs through a 10 KDa or 1000 KDa pore size filter. The final product, composed of secreted EVs and concentrated CM, is formulated in PlasmaLyte A and stored frozen. The frozen final product is ready to use for direct subconjunctival injection or topical delivery after thawing.

Concentration: 2 mg/mL for the 10 KDa method; 0.5 mg/mL for the 1000 KDa method.

Particle concentration: $1.0 \times 10^{11}$ particles/ml for the 10 KDa method; $5.0 \times 10^{10}$ particles/ml for the 1000 KDa method.

B) MSC-EVs

Extracellular vesicles originating from human bone marrow mesenchymal stem cells (MSC-EVs) are obtained after filtering MSC CM containing EVs through a 10 KDa pore size filter following a similar process as for CDC-EV production. MSC-EVs are a non-cellular, filter sterilized product obtained from human MSCs cultured under defined, serum-free conditions. The final product, composed of secreted EVs and concentrated CM, is formulated in PlasmaLyte A and stored frozen. The frozen final product is "ready to use" for direct subconjunctival injection after thawing.

C) Newt-EVs

Extracellular vesicles originating from newt A1 cell line (Newt-EVs) are obtained after filtering A1 cell line CM containing EVs through a 10 KDa pore size filter following a similar process as for CDC-EV production. Newt-EVs are a non-cellular, filter sterilized product obtained from newt A1 cells cultured under defined, serum-free conditions. The final product, composed of secreted EVs and concentrated CM, is formulated in PlasmaLyte A and stored frozen. The frozen final product is ready to use for direct subconjunctival injection after thawing.

Example 4: Exosome Labeling

Some of the exosome samples were further isolated using ultracentrifugation. After the conditioned medium was concentrated, the exosomes were labelled with DiR lipophilic dye in the specified dilution. The samples were placed in the 37° C. incubator for 30 minutes. The samples were resuspended in ~3.5 mL of Plasmalyte and were loaded into ultracentrifuge tubes (11×60 mm tubes). The samples were weighed before centrifugation to ensure that all weights were equivalent. The samples were spun at 110,000 g (39,300 rpm using Beckman Coulter SW 60Ti Rotor) for 70 minutes. After the samples were finished spinning, the supernatant was removed from each tube and was discarded. The remaining pellet was resuspended by vortexing and sonicating briefly in 1 mL of Plasmalyte. Afterwards, 2.5 mL of Plasmalyte was added and the samples were vortexed and sonicated again. The samples were spun a second time at 110,000 g for another 70 minutes. After the second spin, the remaining supernatant was saved as the free dye vehicle. The samples were resuspended again by vortexing and sonicating briefly in 1 mL of Plasmalyte, followed by a second round of resuspension in 2.5 mL of Plasmalyte. A small sample was used to measure particle count on the Nanosight. Once particle count was calculated, the samples were normalized to ~2e10 particles/mL Example 5: Biodistribution The exosomes were fluorescently labelled with a fluorescent dye (DiR; 1,1'-dioctadecyl-3,3,3',3'-tetramethylindo tricarbocyanine iodide) at the noted dilutions. DiR labelled CDC-exosomes isolated using the PEG precipitation protocol (see Example 3) or the UFC protocol were subcutaneously injected into the back of 6 SCID mice (3 mice injected with PEG isolated exosomes and 3 mice injected with UFC isolated exosomes). Before administration, 2 wounds were produced in the back of the mice using a 5 mm diameter puncture. The PEG or UFC exosomes were subcutaneously injected in the left wound and PBS in the right wound. Injection of exosomes into the surrounding areas around the wound showed DiR signal when monitored on the IVIS bioimager 24 hours after administration, as shown in FIG. 1.

Figure 2A:
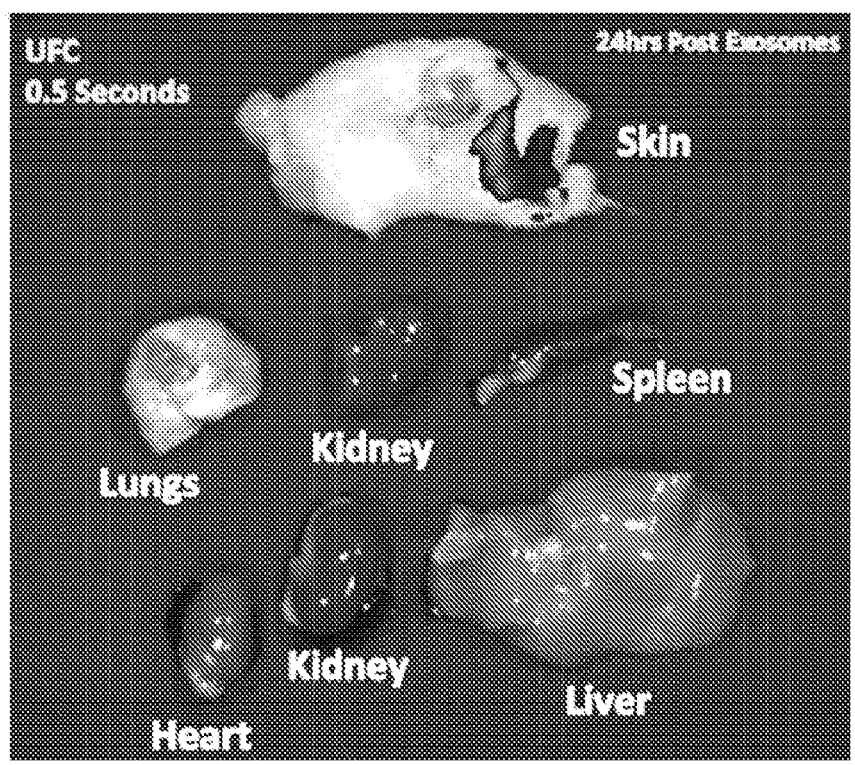
FIGS. 2A-B show biodistribution and retention of DiR labelled exosomes in various organs 24 hours after subcutaneous injection into the back of mice.
Figure 2B:
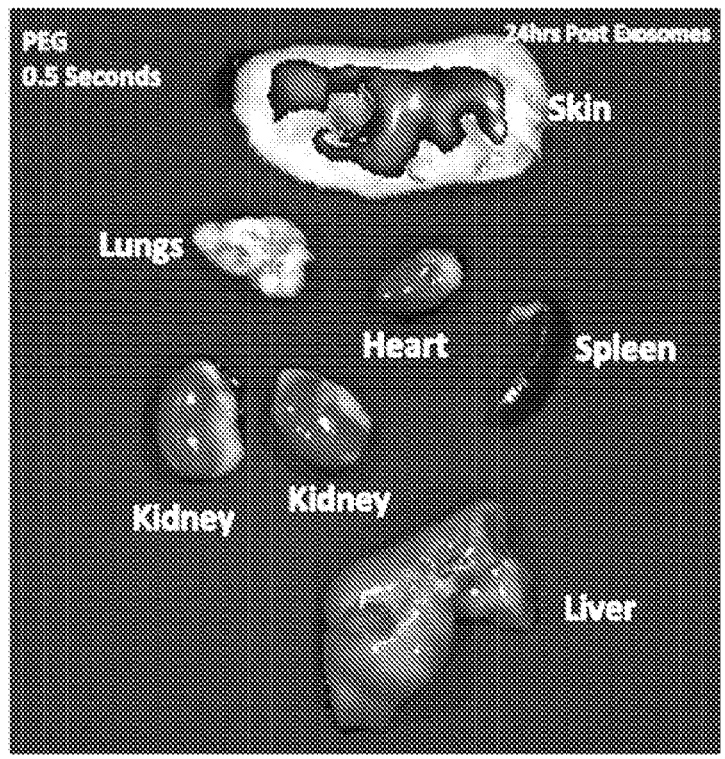

As shown in FIGS. 2A-B, ex vivo imaging of each mouse's internal organs showed no fluorescence, and DiR positive signal was only observed in the skin.

Example 6: Experimental Design (1st Experiment)

36 female Balb/c mice were randomized into 3 treatment groups of 12 animals each following acclimation. The mice were prepared for irradiation by removal of the hair on the entire back 2 days prior to radiation exposure (Day −2) using an electric shaver and depilatory cream. Dermatitis was induced by ionizing radiation administered as 6×10Gy fractions given on Days 0-2 and Days 5-7. The total accumulated dose was 60 Gy. On Days 0-2 and Days 5-7, the mice were anesthetized using xylazine (5 mg/kg) and ketamine (100 mg/kg) given by intraperitoneal injection. The mice were placed on a 4-mm polymethyl methacrylate plate and two 27G needles were used to secure the dorsal skin during irradiation. A lead shield containing a window cut out of its base was placed over the animal so that an area of skin about 2 cm×4 cm in size was left exposed for irradiation. Radiation was generated by a 160 kVp (15-ma) X-ray source at a focal distance of 30 cm, hardened with a 0.35 mm Cu filtration system at a rate of 3.2 Gy/minute.

Figure 3:
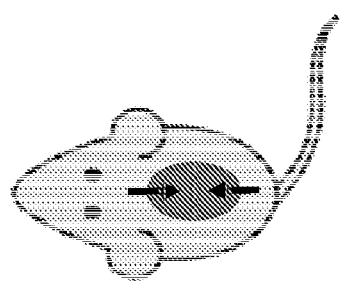
FIG. 3 is a dosing diagram.

For treatment, all animals were dosed via subcutaneous administration of 2 injections of 0.1 mL volume released directly under the irradiated area so as to maximally cover the area. Each dose was delivered using two entry sites, one caudal and one rostral, originating outside the radiation/dermatitis zone, and tunnelling to dose under radiation exposure area, so that this entire area was uniformly and thoroughly covered, as illustrated in FIG. 3. A new needle was used for each animal.

Figure 4:
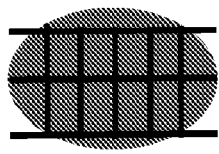
FIG. 4 is a skin collection diagram.
Figure 4A:
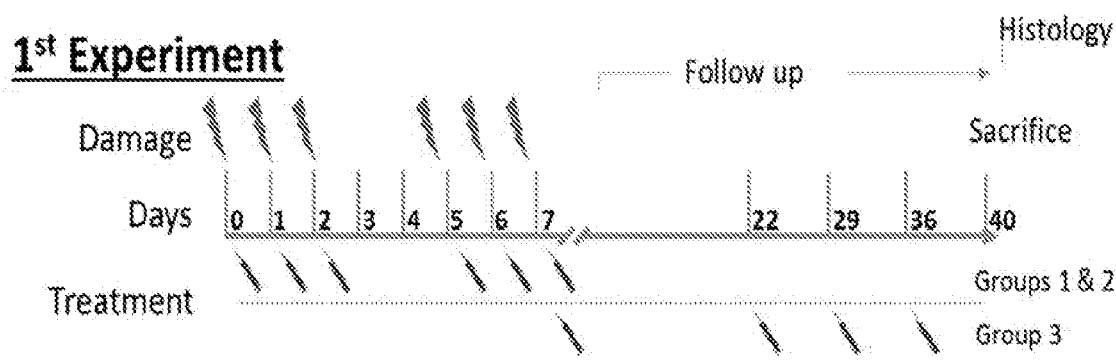
FIG. 4A schematically shows the study design for $1^{st}$ Experiment

Group 1 mice were administered vehicle to match each administered dose of exosomes. The animals in Group 2 were administered a low dose of exosomes (0.25 mg/mL; total 300 µg) less than 1 hour post radiation exposure on each radiation day (Days 0-2 and Days 5-7). Group 3 mice were administered a higher dose of exosomes (1.5 mg/mL; total 1200 µg) less than 1 hour post radiation exposure on Day 7, with additional doses administered on Days 22, 29 and 36. FIG. 4A and Table 1A show the details of the study design for 1st Experiment.

TABLE 4A

| Group | Number of animals (Balb/c) | Fractionated radiation 60 Gy (6 × 10 Gy) | Treatment* (s.c.) volume 2 × 0.1 mL | Schedule | Clinical Derm Eval/Photo | Endpoints | Endpoint collections |
|---|---|---|---|---|---|---|---|
| 1 | 12/female | 10 Gy Days 0-2 Days 5-7 | Vehicle | Days 0-2 Days 5-7 | Every other day Day 4-40 | 1 mouse Day 26 | Dermatitis skin samples: |
| 2 | | | CDC-EVs low dose 0.25 mg/mL | Days 0-2 Days 5-7 | | Day 28 2 mice Day 36 | 4 pieces in cassettes in 10% NBF |
| 3 | | | CDC-EVs high dose 1.5 mg/mL | Day 7 Day 22 Day 29 Day 36 | | Day 40 | 4 pieces snap frozen |

*All dosing was performed <1 hour post radiation; subcutaneous dosing was performed in two doses of 0.1 mL using long needle with entry site outside radiation/dermatitis zone, and tunneling to central point of radiation area, as illustrated in FIG. 3.

Dermatitis severity was evaluated clinically and in a blinded manner starting on Day 4 and continuing every other day until study completion on Day 40. For evaluation of dermatitis, a score was assigned visually on each day of evaluation, and a digital photograph of each animal was taken and scored at the completion of the study based on an established scoring scale by two trained blinded observers. The average of these two scores was the final Blinded Score. Any animal receiving a score of 5 received buprenorphine twice each day (b.i.d) until the score was less than 5.

On Day 40, all animals were euthanized by $CO_2$ asphyxiation. Skin was collected from the irradiated region: 4 pieces were stored in 10% neutral buffered formalin in histology cassettes, and 4 pieces were snap frozen. Data was analyzed using GraphPad Prism 6.07.

Example 7: Animal Identification, Housing, and Diet (1st Experiment)

Female Balb/c mice (Strain Code 028, Charles River Laboratories), aged ~5-7 weeks, with average body weight (±SD) of 17.18±1.24 g at study start (Day −2), were used. The mice were acclimated at least 3 days prior to study commencement. During this period, the mice were observed daily in order to reject any animals that were in poor condition.

The study was performed in animal rooms provided with filtered air at a temperature of 70±5° F. and 50±20% relative humidity. The animal rooms were set to maintain a minimum of 12 to 15 air changes per hour. The room was on an automatic timer for a light/dark cycle of 12 hours on and 12 hours off with no twilight.

The mice were fed with Labdiet® 5053-certified PicoLab rodent diet. Food and water were provided ad libitum.

Example 8: Endpoints (1st Experiment)

In order to compare differences between Groups at various points in the study, 1 mouse from each Group, representative of mean clinical dermatitis score on that day, was euthanized on Days 26 and 28, and 2 mice from each Group were sacrificed prior to injection on Day 36. All surviving animals were euthanized by $CO_2$ asphyxiation on Day 40. For all endpoints, 8 pieces of skin were collected from the irradiated region: 4 pieces were stored in 10% neutral buffered formalin in histology cassettes, and 4 pieces were snap frozen, as illustrated in FIG. 4.

Example 9: Weight Change Evaluation ($1^{st}$ Experiment)

Figure 5:
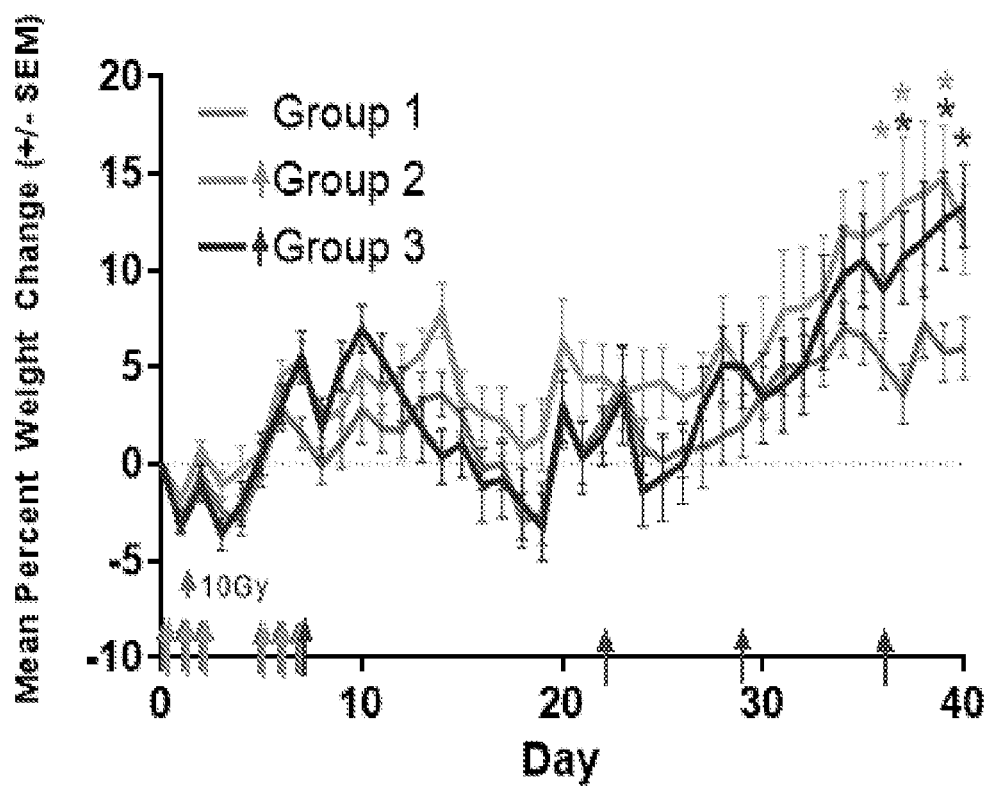
FIG. 5 shows the mean daily percent body weight change of the experimental animals, for $1^{st}$ Experiment.
Figure 6:
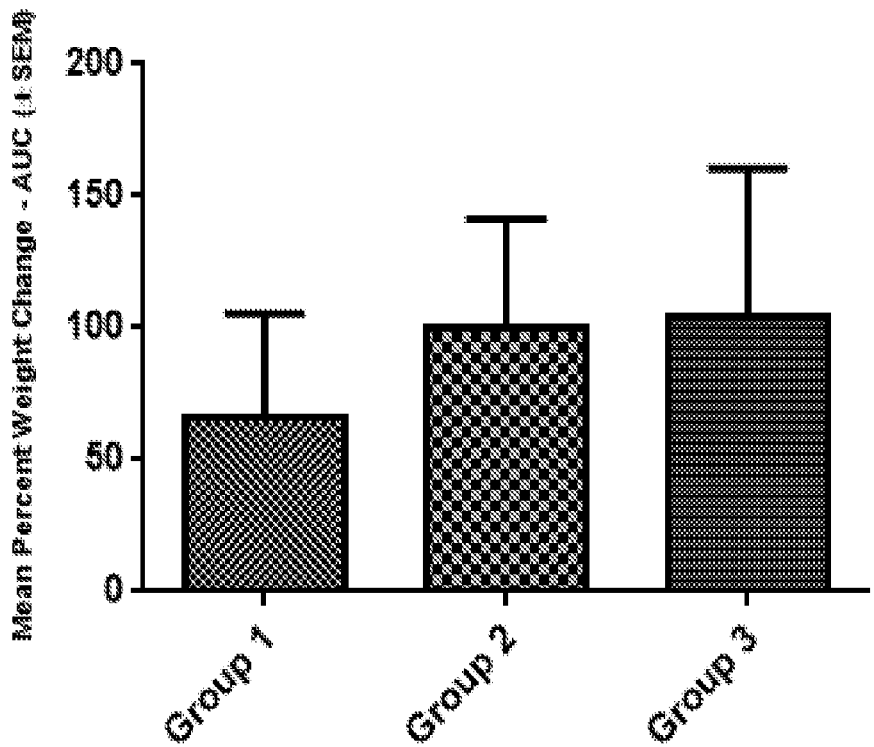
FIG. 6 shows cumulative mean daily mean weight change of the experimental animals over the complete course of the study, for Pt Experiment.

The mice displayed a typical pattern of radiation-inhibited weight gain for the model. The mean weight of each Group tracked together similarly on Days 0-35. On Days 36-40 of the study (late recovery), however, the mean weight of the animals treated with either low-dose exosomes (Group 2) or high-dose exosomes (Group 3) was significantly greater than those that of the vehicle control animals (Group 1) on 4 out of 5 of those days, as assessed by unpaired two-tailed Student's T-test, constituting a trend that suggests an effect of the exosomes on weight gain following fractionated radiation exposure. The mean daily percent body weight change±SEM is shown in FIG. 5, wherein the arrows indicate days of radiation exposure for Groups 1-3, or dosing of exosomes (Groups 2-3) or vehicle (Group 1), and wherein unpaired, two-tailed Student's t-test was used to determine statistically significant differences for each of Days 30-40 of the study (late recovery). AUC was calculated using the trapezoidal rule transformation to assess cumulative daily mean weight change over the complete course of the study, and the AUC data are shown in FIG. 6.

Example 10: Clinical Dermatitis Scoring ($1^{st}$ Experiment)

Starting on Day 4 and continuing every other day thereafter (Days 4-40), each animal was evaluated for radiation-induced dermatitis and photographed for subsequent blinded scoring of dermatitis at the completion of the study. For the evaluation of dermatitis, the animals were anesthetized with inhalation anesthetics, and the skin was photographed. Dermatitis was scored visually by comparison to a validated photographic scale, ranging from 0 for normal, to 5 for severe ulceration (clinical scoring), as defined in Table 2.

TABLE 2

| Score | Description |
|---|---|
| 0 | normal, no changes |
| 1 | mild erythema |
| 2 | moderate to severe erythema, slight desquamation |
| 3 | Desquamation of 25-50% of the irradiated area |
| 4 | Desquamation in >50% of irradiated area |
| 5 | Frank ulcer |

A score of 1-2 is considered to represent a mild stage of the disease, whereas a score of 3-5 is considered to indicate moderate to severe dermatitis. Following this preliminary clinical scoring, a photograph was taken of each animal's skin using a standardized technique. If the animals received a score of 5, or displayed pain-associated behavior, all animals enrolled in the study were to receive equivalent buprenorphine subcutaneous injection (outside the irradiated area) of 0.05-0.1 mg/kg BID for 24 hours or until pain or ulceration was resolved.

At the conclusion of the experiment, the photographs were randomly numbered for blinded scoring. Thereafter, 2 independent trained observers graded the photographs in a blinded fashion and based on the previously established reference photographs and the scoring table as defined in Table 2. For each photograph, the actual blinded score was derived using the average of the evaluator's scores.

Figure 7:
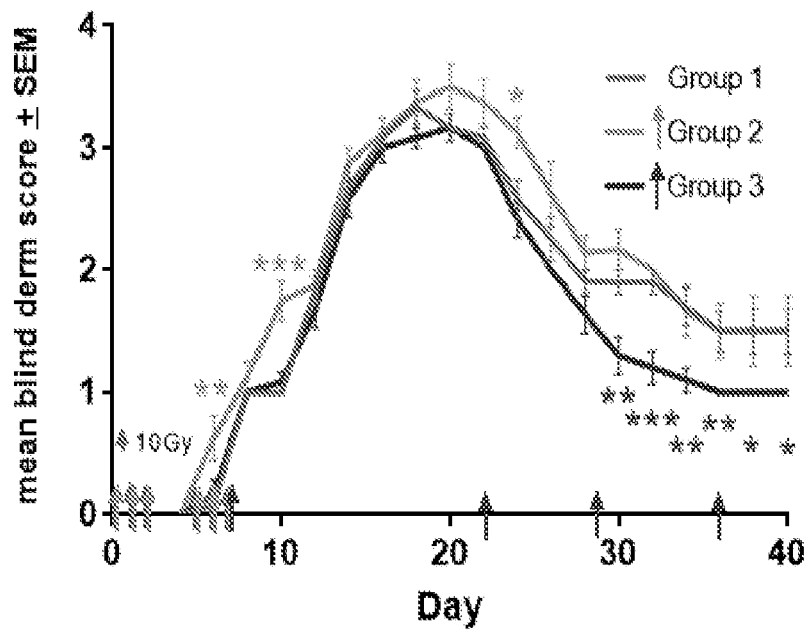
FIG. 7 and FIG. 7A show the mean daily blinded dermatitis scores of the experimental animals, for $1^{st}$ Experiment.
Figure 7A:
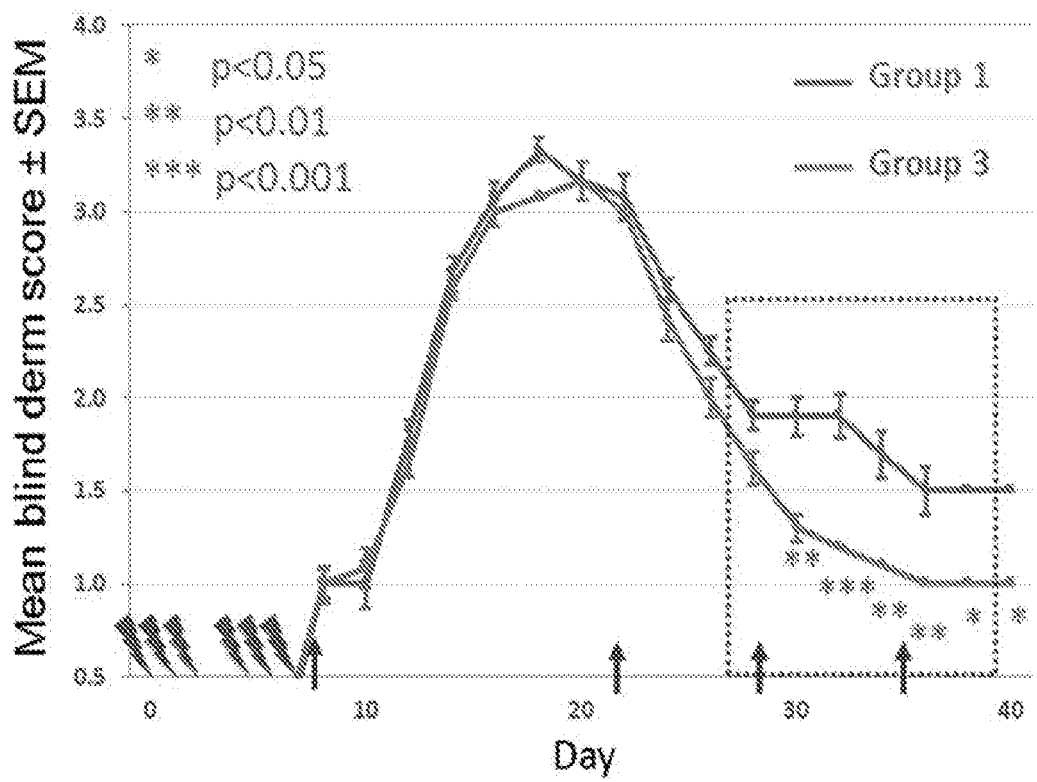
Figure 8:
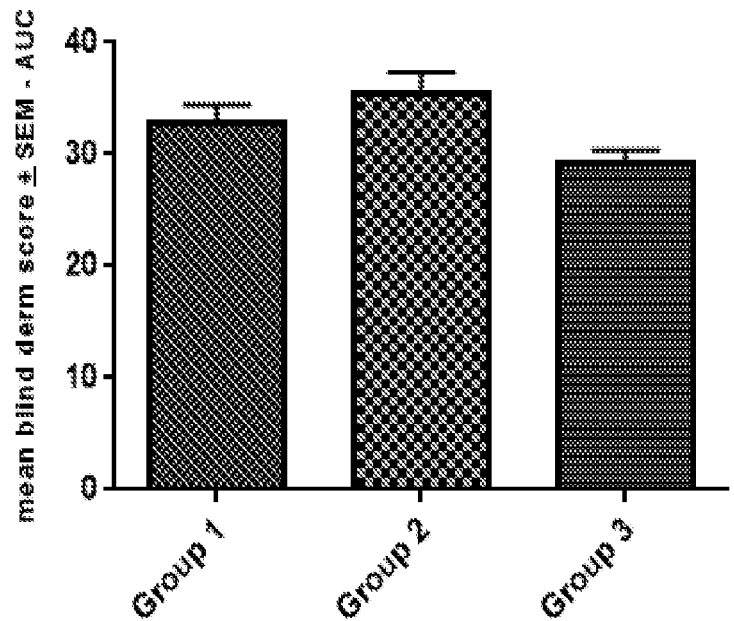
FIG. 8 shows cumulative mean daily mean blinded dermatitis scores of the experimental animals over the complete course of the study, for $1^{st}$ Experiment.

Average blinded skin damage scores for each evaluation day are shown in FIG. 7 and FIG. 7A, and AUC was calculated using the trapezoidal rule in order to assess cumulative differences in dermatitis between Groups 1-3, as shown in FIG. 8. The animals in Group 1 (vehicle control) displayed a pattern of dermatitis and partial recovery that is typical for the model. On Days 30-40, during the late-recovery phase of radiation-induced dermatitis, the animals in Group 3 (high-dose exosomes) displayed statistically significant lower mean dermatitis scores than the animals in Group 1 (vehicle control) on each day of evaluation tested by unpaired two-tailed Student's t-test.

This data indicates that high-dose exosomes, when administered as indicated, is efficacious in improving resolution of dermatitis following fractionated-radiation exposure in this model, and strongly suggests that high-dose exosomes may promote similar beneficial effects in clinical settings.

Example 11: Dermatitis Severity by Day and Therapeutic Efficacy of Treatment ($1^{st}$ Experiment)

An analysis of the severity of dermatitis on each evaluation day was performed using the Mann-Whitney rank-sum analysis to compare the blind scores for each treatment group to the vehicle control group on each day of the analysis. The results of this analysis are shown in FIG. 9, wherein green shading (Group 3 at Days 30, 32, 34, and 36) indicates improvement, and red shading (Group 2 at Days 6, 10 and 24) indicates exacerbation of damage, compared to Group 1 (vehicle control) on the indicated day, and wherein bold font denotes significant difference in skin damage scores, red arrows indicate radiation exposures (10Gy each), light blue arrows indicate dosing with low-dose exosomes (Group 2), and dark blue arrows indicate dosing with high-dose exosomes (Group 3). At least 2 days of statistically significant improvement in dermatitis score compared to controls are required before the observation can be regarded as therapeutically meaningful. The animals treated with high-dose exosomes (Group 3) displayed a trend of significantly improved dermatitis score compared to Group 1 (vehicle control) beginning at evaluation Day 30 and continuing through Day 36, a trend of 4 days in a row, indicating that the exosome treatment resulted in a therapeutically meaningful improvement in resolution of dermatitis following fractionated radiation exposure. The animals treated with low-dose exosomes (Group 2) exacerbated dermatitis on 3 isolated days (Day 6, Day 10 and Day 24) of the study.

Example 12: Duration of Severe Dermatitis ($1^{st}$ Experiment)

A dermatitis score of greater than 2 is considered severe dermatitis (SD). In order to compare the duration of SD induced by fractionated radiation between the treatment groups over the complete course of the study, the total number of days in which each animal displayed mean SD scores of >2 versus ≤2 were compared using Fischer's Exact test, as shown in Table 3.

TABLE 3

| Group | Number of >2 days | Number of ≤2 days | Total animal days | % of number of >2 days | p value |
|---|---|---|---|---|---|
| 1 | 66 | 145 | 211 | 31.28 | — |
| 2 | 53 | 82 | 135 | 39.26 | 0.1332 |
| 3 | 59 | 152 | 211 | 27.96 | 0.5225 |

Example 13: Percentage of Animals with Severe Dermatitis by Day (1$^{st}$ Experiment)

The percentage of animals in each group with severe dermatitis (score >2) at each day of evaluation is shown in FIG. 10. This evaluation is used to ascertain when in the course of the study various treatments exert maximal impact on the pathology of dermatitis induced by fractionated radiation. For the animals treated with low-dose exosomes (Group 2), a higher percentage of the animals displayed severe dermatitis compared to the vehicle controls (Group 1) on Day 14 and Days 24-30 of the study, as indicated by red shading in FIG. 10. For the animals treated with high-dose exosomes (Group 3), a lower percentage of the animals displayed severe dermatitis compared to the vehicle controls (Group 1) on Day 16, and Days 24 and 26, as indicated by green shading in FIG. 10.

Conclusions from 1$^{st}$ Experiment

From Day 36-40 of the study (late recovery), the mean weight of animals treated with either low-dose (0.25 mg/mL) or high-dose (1.5 mg/mL) CDC-EVs was significantly greater than that of the vehicle control mice on four out of five of those days, indicating that CDC-EVs enhanced weight gain following fractionated radiation exposure.

From Day 30-40 of the study (late-recovery), the mice treated with high-dose (1.5 mg/mL) CDC-EVs displayed statistically significant lower mean dermatitis scores than the vehicle treated mice, indicating that high-dose CDC-EVs improved resolution of dermatitis following fractionated radiation exposure.

Rank-sum analysis found that the mice treated with high-dose CDC-EVs displayed a trend of significantly improved dermatitis score compared to the vehicle control beginning at evaluation Day 30 and continuing through Day 36, a trend of four days in a row, indicating that CDC-EV treatment resulted in a therapeutically meaningful improvement in resolution of dermatitis following fractionated radiation exposure.

For the mice treated with low-dose CDC-EVs, a higher percentage of the mice displayed severe dermatitis compared to the vehicle controls on Day 14 and Days 24-30 of the study. For the mice treated with high-dose CDC-EVs, a lower percentage of the mice displayed severe dermatitis on Day 16, and Day 24-26.

Example 14: Experimental Design (2$^{nd}$ Experiment)

48 female Balb/c mice were randomized into 4 treatment groups of 12 animals each following acclimation. The mice were prepared for radiation by removal of the hair on the entire back two days prior to radiation (Day −2) using an electric shaver and depilatory cream. Dermatitis was induced by ionizing radiation administered as 6×10Gy fractions given on Days 0-2 and Days 5-7. The total accumulated dose was 60 Gy. On Days 0-2 and Days 5-7, the mice were anesthetized using xylazine (5 mg/kg) and ketamine (100 mg/kg) given by intraperitoneal injection. The mice were then placed on a 4-mm polymethyl methacrylate plate and two 27G needles were used to secure the dorsal skin during irradiation. A lead shield containing a window cut out of its base was placed over the animal so that an area of skin about 2 cm×4 cm in size was exposed and the skin was irradiated. Radiation was generated by a 160 kVp (15-ma) X-ray source at a focal distance of 30 cm, hardened with a 0.35 mm Cu filtration system at a rate of 3.2 Gy/minute.

Animals were dosed via subcutaneous injection (s.c.) of 2×0.1 mL vol. with vehicle (PlasmaLyte; Group 1), low-dose test article (CDC-EVs at 0.75 mg/mL; Group 2), or high-dose test article (CDC-EVs at 1.5 mg/mL; Group 3) respectively, every seven days (Q7D) beginning on study Day 14, with additional administrations on Days 21, 28, and 35. Group 4 animals were administered a single high-dose CDC-EVs of 1.5 mg/mL on Day 21 only. Long needles were used for dosing, with entry outside the area of radiation exposure. Needles were used to provide dosing originating at two entry sites, one caudal and one rostral, each outside the radiation/dermatitis zone, and tunneling to dose under the radiation exposure area, so that this entire area was uniformly and thoroughly covered, as illustrated in FIG. 3. A new needle was used for each animal.

Dermatitis severity was evaluated clinically and in a blinded manner starting on Day 4 and continuing every other day until study completion on Day 36. For evaluation of dermatitis, a score was assigned visually on each day of evaluation, and a digital photograph of each animal was taken and scored at the completion of the study based on an established scoring scale by two blinded observers, and the average of these two scores considered for analysis. Animals receiving a score of 5 received buprenorphine twice each day (b.i.d) until the score dropped below 5.

Figure 11:
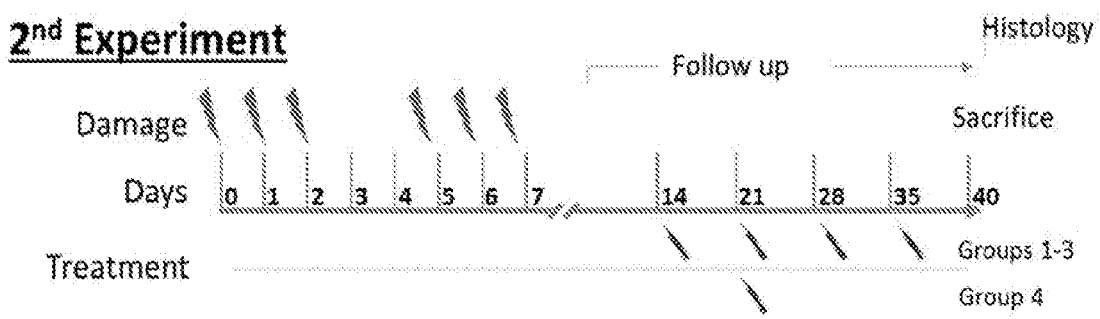
FIG. 11 schematically shows the study design for $2^{nd}$ Experiment

On Days 28 and 35, two animals from each Group were sacrificed and serum collected via Microtainer™ SST tubes and skin collected as indicated below. On Day 40, all remaining animals were euthanized by $CO_2$ asphyxiation. For each animal sacrificed, skin was collected from the irradiated region and 4 pieces stored in 10% neutral buffered formalin (NBF) in histology cassettes, and 4 pieces snap frozen. FIG. 11 and Table 4 show the details of the study design for 1$^{st}$ Experiment.

TABLE 4

| Group | Number of animals (Balb/c) | Fractionated radiation 60 Gy (6 × 10 Gy) | Treatment* (s.c.) volume 2 × 0.1 mL | Schedule | Clinical Derm Eval/Photo | Endpoints | Endpoint collections |
|---|---|---|---|---|---|---|---|
| 1 2 | 12/female | 10 Gy Days 0-2 Days 5-7 | Vehicle CDC-EVs low dose 0.75 mg/mL | Q7D Days 14, 21, 28, 35 | Every other day Day 4-40 | 2 mice Day 28 2 mice Day 35 | Serum via terminal bleed Dermatitis |

TABLE 4-continued

| Group | Number of animals (Balb/c) | Fractionated radiation 60 Gy (6 × 10 Gy) | Treatment* (s.c.) volume 2 × 0.1 mL | Schedule | Clinical Derm Eval/Photo | Endpoints | Endpoint collections |
|---|---|---|---|---|---|---|---|
| 3 | | | CDC-EVs high dose 1.5 mg/mL | | | All others Day 40 | skin samples: 4 pieces in cassettes in 10% NBF 4 pieces snap frozen |
| 4 | | | CDC-EVs high dose 1.5 mg/mL | Single dose Day 21 | | | |

*All dosing was performed <1 hour post radiation; subcutaneous dosing was performed in two doses of 0.1 mL using long needle with entry site outside radiation/dermatitis zone, and tunneling to central point of radiation area, as illustrated in FIG. 3.

Example 15: Animal Identification, Housing, and Diet ($2^{nd}$ Experiment)

Female Balb/c mice (Taconic Biosciences), aged ~6 weeks, with average body weight (±SD) of 16.83±1.23 g at study start (Day −2), were used. The mice were acclimated at least 3 days prior to study commencement. During this period, the mice were observed daily in order to reject any animals that were in poor condition.

The study was performed in animal rooms provided with filtered air at a temperature of 70±5° F. and 50±20% relative humidity. The animal rooms were set to maintain a minimum of 12 to 15 air changes per hour. The room was on an automatic timer for a light/dark cycle of 12 hours on and 12 hours off with no twilight.

The mice were fed with Labdiet® 5053-certified PicoLab rodent diet. Food and water were provided ad libitum.

Example 16: Endpoints ($2^{nd}$ Experiment)

In order to compare differences between Groups at various points in the study, 2 mice from each Group, representative of mean clinical dermatitis score on that day, were euthanized on Days 28 and 35. All surviving animals were euthanized by $CO_2$ asphyxiation on Day 40. For all endpoints, 8 pieces of skin were collected from the irradiated region: 4 pieces were stored in 10% neutral buffered formalin in histology cassettes, and 4 pieces were snap frozen, as illustrated in FIG. 4.

Example 17: Weight Change Evaluation ($2^{nd}$ Experiment)

Figure 12:
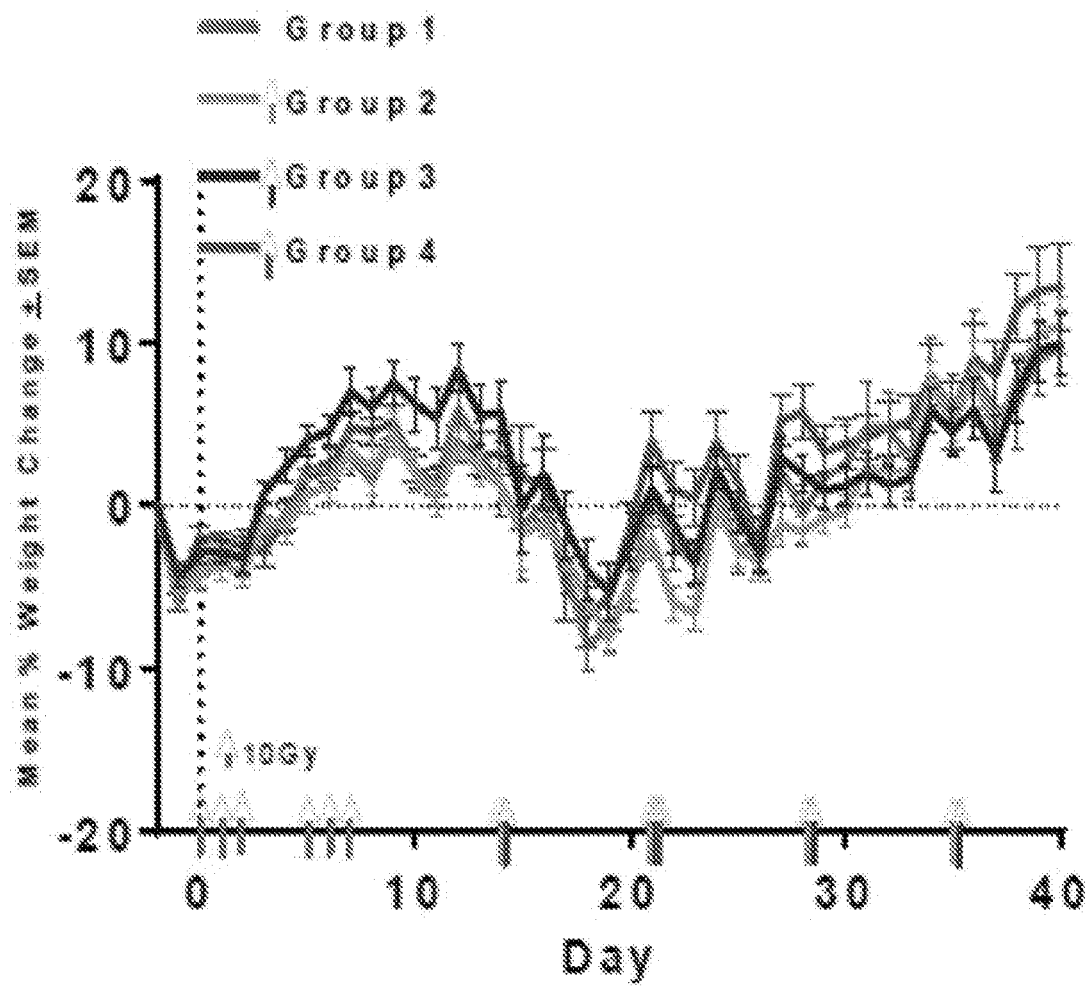
FIG. 12 shows the mean daily percent body weight change of the experimental animals, for $2^{nd}$ Experiment.

The mice displayed a typical pattern of weight change usually observed in the fractionated radiation-induced dermatitis model; an initial gain in weight over the first ~10-12 days followed by a brief period of weight loss due to radiation exposure (Days 0-2 and 5-7) manifesting at Day ~12-20, and finally a slow and steady pattern of weight recovery and ultimately weight gain. The mean percentage of weight change of each Group tracked similarly together from study Day 0-40. The mean daily percent body weight changes±SEM are shown in FIG. 12.

Figure 13:
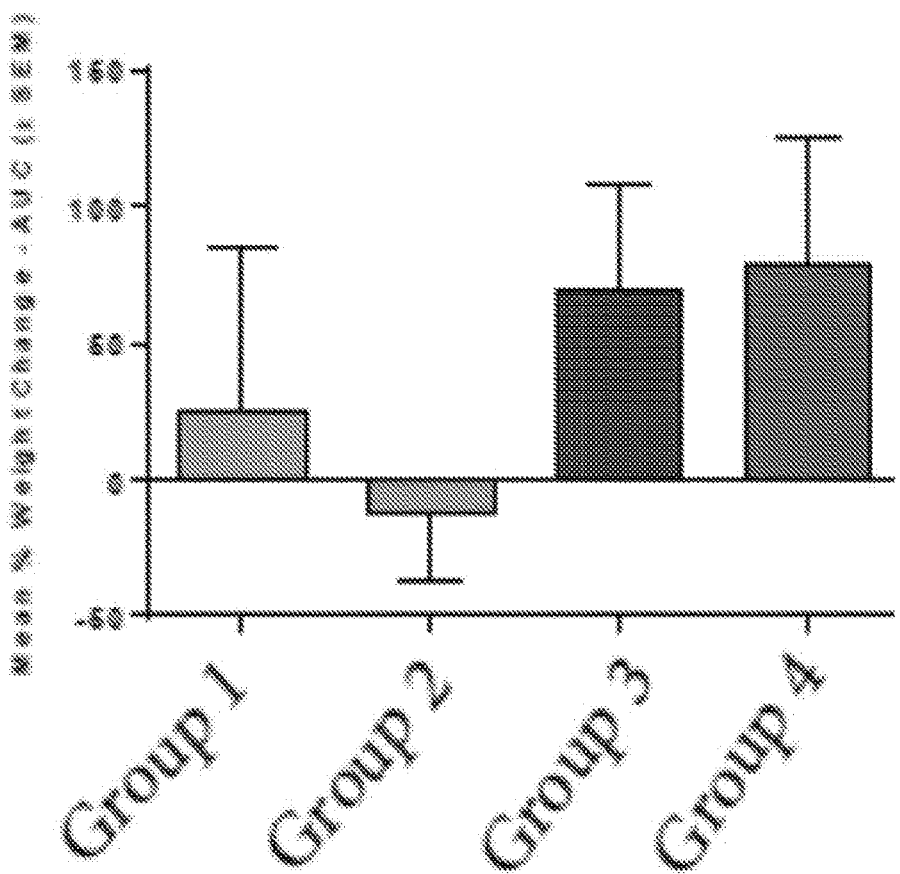
FIG. 13 shows cumulative mean daily mean weight change of the experimental animals over the complete course of the study, for $2^{nd}$ Experiment.

To determine whether there were any statistically significant differences in cumulative body weight change of CDC-EV treated animals compared to vehicle treated animals, the area under the curve (AUC) was determined using the trapezoidal rule transformation. Statistical evaluation was performed using one-way ANOVA and Dunnett's Multiple Comparison post hoc test. The AUC data are shown in FIG. 13.

Example 18: Clinical Dermatitis Scoring ($2^{nd}$ Experiment)

The same procedure as described in Example 10 was employed for 2nd Experiment.

Figure 14A:
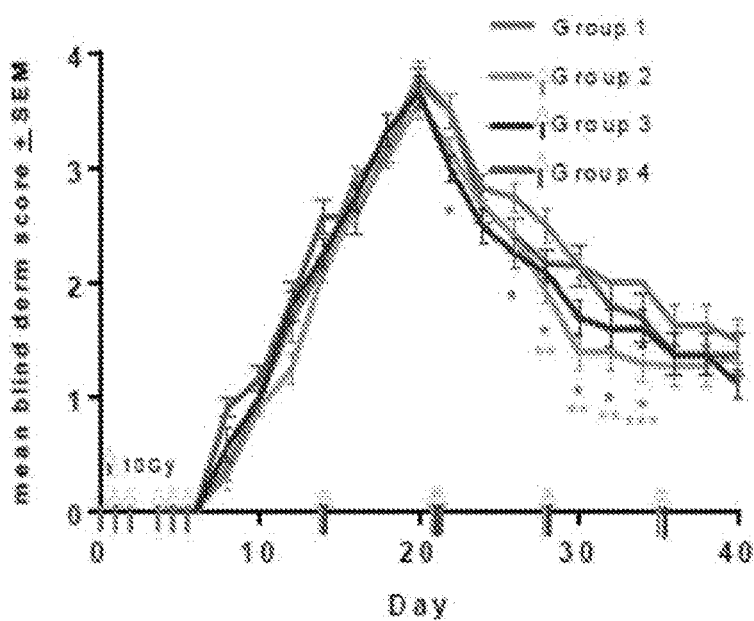
FIGS. 14A-B show the mean daily blinded dermatitis scores of the experimental animals, for $2^{nd}$ Experiment.
Figure 14B:
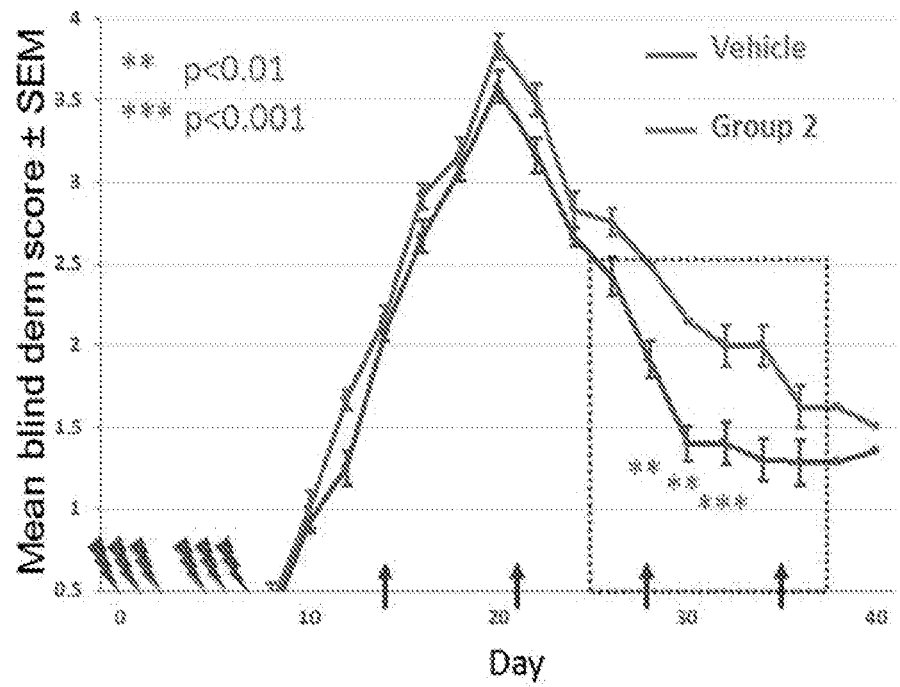
Figure 15:
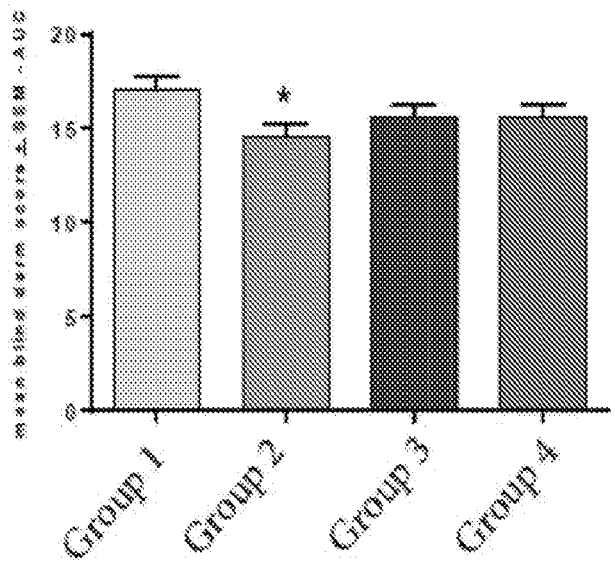
FIG. 15 shows cumulative mean daily mean blinded dermatitis scores of the experimental animals over the complete course of the study, for $2^{nd}$ Experiment.

The blinded mean skin damage scores for each evaluation day are shown in FIGS. 14A-B. Vehicle control animals displayed a pattern of increasing dermatitis peaking at Day 20 followed by partial recovery that is typical for the model. During the recovery phase of radiation-induced dermatitis, animals treated every seven days beginning on Day 14 with high dose (1.5 mg/mL; Group 3) or low-dose (0.75 mg/mL; Group 2) CDC-EVs showed statistically significant lower mean dermatitis scores than vehicle treated animals on several days when tested by unpaired two-tailed Student's t-test. Animals administered a single high-dose (1.5 mg/mL; Group 4)) of CDC-EVs on Day 21 did not display a statistically significant improved mean dermatitis score compared to control on any evaluation day of the study. In order to assess cumulative differences in dermatitis between Groups 1-4, the AUC was calculated using the trapezoidal approximation, as shown in FIG. 15. Statistical evaluation was tested by one-way ANOVA and Dunnett's Multiple Comparison post hoc test. Administration of low-dose (0.75 mg/mL; Group 2) CDC-EVs resulted in a statistically significant improved mean cumulative dermatitis score over the full course of the study (Day 4-40) (mean diff.=2.531; 95% CI of diff=0.2207 to 4.842).

This data indicates that CDC-EVs, when administered as indicated, are efficacious in aiding resolution in this model of fractionated radiation-induced dermatitis, and suggests that CDC-EVs may promote similar beneficial effects in clinical settings.

Example 19: Dermatitis Severity by Day and Therapeutic Efficacy of Treatment ($2^{nd}$ Experiment)

Differences in dermatitis severity between Groups was tested using the Mann-Whitney rank sum analysis to compare the blind scores for each treatment group to the vehicle control group on each evaluation day of the study. The results of this analysis are shown in FIG. 16. At least two days of statistically significant improvement in dermatitis score compared to controls are required before the observation can be regarded as therapeutically meaningful. Animals treated with low-dose 0.75 mg/mL CDC-EVs (Group 2) displayed a significantly improved dermatitis score compared to the vehicle control (Group 1) over six consecutive days beginning at evaluation Day 28 and continuing through Day 34, a trend of four days in a row, indicating a therapeutically meaningful improvement in dermatitis during this portion of the study. The mice treated with high-dose 1.5 mg/mL CDC-EVs (Group 3) every seven days beginning on Day 14 displayed a statistically significant improvement in dermatitis score on two nonconsecutive days (Day 22 and Day 26) of the study. Administration of a single high-dose of CDC-EVs (Group 4) on Day 21 did not result in a statistically significant improvement in dermatitis score compared to vehicle administered animals on any evaluation day.

These results indicate therapeutic efficacy of low-dose CDC-EVs (Group 2) in enhancing resolution of fractionated radiation-induced dermatitis when administered as indicated in this preclinical model, and suggest that CDC-EVs may likewise improve the kinetics of dermatitis resolution following fractionated radiation administered in clinical settings.

Example 20: Duration of Severe Dermatitis ($2^{nd}$ Experiment)

Figure 17:
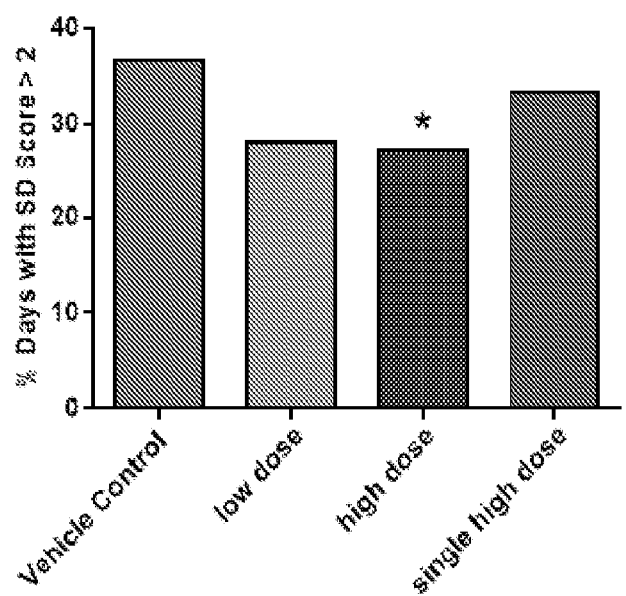
FIG. 17 is a graphical representation of FIG. 16 data depicting percentage of animal days with severe dermatitis (DS>2) over the full course of the study.

A dermatitis score of greater than 2 is considered severe dermatitis (SD). In order to compare the duration of SD induced by fractionated radiation between treatment groups over the complete course of the study, the total days in which each animals displayed mean SD scores of >2 versus ≤2 were compared using Fischer's Exact test, as shown in Table 5 and FIG. 17.

TABLE 5

| Group | Number of >2 days | Number of ≤2 days | Total animal days | % of number of >2 days | p value |
|---|---|---|---|---|---|
| 1 | 77 | 133 | 210 | 36.67 | — |
| 2 | 58 | 149 | 207 | 28.02 | 0.0607 |
| 3 | 57 | 153 | 210 | 27.14 | 0.0465* |
| 4 | 70 | 140 | 210 | 33.33 | 0.5394 |

*= p < 0.05

Animals administered high-dose 1.5 mg/mL CDC-EVs (Group 3) every seven days beginning on Day 14 displayed a statistically significant reduction in the number of animal-days of severe dermatitis (27.14% of evaluation days) compared with animals administered vehicle on the same schedule (36.67% of evaluation days) (p=0.0465).

These data indicate that high-dose CDC-EVs mitigates the duration of severe dermatitis as administered in this preclinical model, and suggests that CDC-EVs may likewise decrease the duration of severe dermatitis in the clinical setting.

Example 21: Percentage of Animals with Severe Dermatitis by Day ($2^{nd}$ Experiment)

Figure 18:
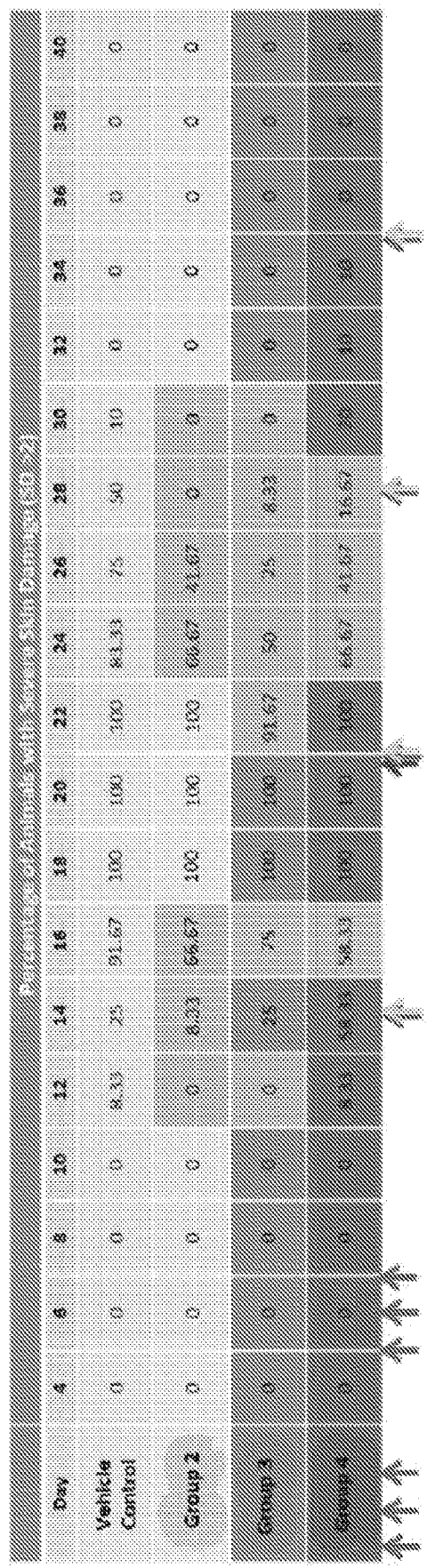
FIG. 18 shows % of the experimental animals with severe skin damages by day, for $2^{nd}$ Experiment.

In order to determine the timing of treatment impact on the pathology of dermatitis induced by fractionated radiation, a comparison was made of the percentage of animals exhibiting severe dermatitis (score >2) in each treatment group compared to animals administered vehicle at each evaluation day, and is shown in FIG. 18. In the group treated with low-dose CDC-EVs (0.75 mg/mL; Group 2) every seven days beginning on Day 14, fewer animals exhibited severe dermatitis compared to those in the vehicle treated Group 1 on evaluation Day 16, as well as on Days 24-30 of the study. Similarly, in the group treated with high-dose CDC-EVs (1.5 mg/mL; Group 3) every seven days beginning on Day 14, fewer animals displayed severe dermatitis on Day 16, as well as over Days 22-30 of the study compared to the vehicle controls. For the group treated with a single high-dose CDC-EVs (1.5 mg/mL; Group 4) on Day 21, fewer animals displayed severe dermatitis over Days 24-28 compared to those in the group administered vehicle, but this group contained one more animal with severe dermatitis compared to the vehicle administered group over Days 30-34.

These results indicate that treatment with CDC-EVs reduces the prevalence of fractionated radiation-induced severe dermatitis over multiple consecutive days in the recovery phase, compared to treatment with vehicle in this model.

Conclusions from $2^{nd}$ Experiment

Treatment with low-dose CDC-EVs (0.75 mg/mL) resulted in a statistically significant improvement in overall mean dermatitis scores compared to the vehicle treated control mice following fractionated radiation exposure of 6 fractions of 10 Gy.

From Day 26-34 of the study (resolution phase), the mice treated with low-dose (0.75 mg/mL) or high-dose (1.5 mg/mL) CDC-EVs exhibited statistically significant reduced mean dermatitis score compared to the vehicle treated mice, indicating that CDC-EVs improved the resolution of dermatitis following fractionated-radiation exposure.

The mice treated with low-dose (0.75 mg/mL) CDC-EVs exhibited a statistically significant reduction in mean dermatitis score compared to the vehicle treated control mice over six consecutive days in the resolution phase, beginning at evaluation Day 28 and continuing through Day 34, indicating that CDC-EV treatment provided a therapeutically meaningful improvement in the resolution of dermatitis following fractionated radiation exposure.

The mice administered high-dose (1.5 mg/mL) CDC-EVs exhibited a statistically significant reduction in the number of animal-days of clinically severe dermatitis compared with the vehicle treated mice (27.14% versus 36.67% of evaluation days), indicating that CDC-EVs mitigated the duration of clinically severe dermatitis.

Fewer mice treated with low-dose (0.75 mg/mL) or high-dose (1.5 mg/mL) CDC-EVs exhibited clinically severe dermatitis over multiple consecutive evaluation days in the resolution phase compared to those treated with vehicle, indicating that in the resolution phase, treatment with CDC-EVs reduced the prevalence of clinically severe dermatitis induced by fractionated radiation compared to treatment with the vehicle.

Example 22: Histopathology Evaluation

Histopathology microscopic evaluation was performed according to the study design as shown in Table 6, wherein the mice from Group 1-3 were necropsied and the skin was collected from the irradiated region: 4 pieces were stored in 10% neutral buffered formalin; 32 slides were cut and stained with hematoxylin-eosin stain (H&E) and 32 with Masson's trichrome stain (Trichrome).

TABLE 6

| Group | Number of animals (Balb/c) examined histopathologically | Fractionated radiation 60 Gy (6 × 10 Gy) | Treatment (s.c.) volume 2 × 0.1 mL | Treatment schedule |
|---|---|---|---|---|
| 1 | 12 | 10 Gy Days 0-2 Days 5-7 | Vehicle | Days 0-2 Days 5-7 |
| 2 | 8 | | Low-dose CDC-EVs (0.25 mg/mL) | |
| 3 | 12 | | High-dose CDC-EVs (1.5 mg/mL) | Days 7, 22, 27, 32, 37 |

The H&E- and Trichrome-stained slides of the skin were examined and histopathological findings were recorded as acanthosis, epidermal necrosis/ulceration, inflammation, adnexalatrophy/follicular ectasia, and dermal/subcutaneous fibrosis. The findings were graded as 0 (normal), 1 (minimal), 2 (mild), 3 (moderate), or 4 (marked).

Incidence data are shown in Table 7.

TABLE 7

| Diagnosis | Severity | Group 1 | Group 2 | Group 3 |
|---|---|---|---|---|
| Number examined | | 12 | 8 | 12 |
| Acanthosis | Moderate | 5 | 4 | 10 |
| | Marked | 7 | 4 | 2 |
| Number examined | | 12 | 8 | 12 |
| Epidermal necrosis/ulceration | Normal | 3 | 3 | 8 |
| | Minimal | 3 | 1 | 3 |
| | Mild | 5 | 3 | |
| | Moderate | 1 | 1 | 1 |
| Number examined | | 12 | 8 | 12 |
| Inflammation | Minimal | 4 | 3 | 6 |
| | Mild | 8 | 5 | 6 |
| Number examined | | 12 | 8 | 12 |
| Adnexal atrophy/follicular ectasia | Moderate | 6 | 5 | 7 |
| | Marked | 6 | 3 | 5 |
| Number examined | | 12 | 8 | 12 |
| Dermal/subcutaneous fibrosis | Moderate | 2 | 2 | 2 |
| | Marked | 10 | 6 | 10 |

Individual animal data are shown in Table 8.

TABLE 8

| Group | Animal number | Acanthosis | Epidermal necrosis/ulceration | Inflammation | Adnexal atrophy/follicular ectasia | Dermal/ subcutaneous fibrosis |
|---|---|---|---|---|---|---|
| 1 | 1 | 4 | 2 | 2 | 4 | 4 |
| | 2 | 4 | 1 | 2 | 4 | 4 |
| | 3 | 3 | 2 | 1 | 3 | 4 |
| | 4 | 4 | 2 | 2 | 4 | 4 |
| | 5 | 3 | 1 | 2 | 4 | 4 |
| | 6 | 3 | 0 | 2 | 3 | 3 |
| | 7 | 3 | 0 | 1 | 4 | 3 |
| | 8 | 3 | 0 | 2 | 3 | 4 |
| | 9 | 4 | 2 | 1 | 3 | 4 |
| | 10 | 4 | 3 | 2 | 3 | 4 |
| | 11 | 4 | 2 | 1 | 4 | 4 |
| | 12 | 4 | 1 | 2 | 3 | 4 |
| 2 | 13 | 4 | 2 | 2 | 4 | 4 |
| | 14 | 3 | 0 | 1 | 3 | 3 |
| | 15 | 3 | 0 | 2 | 3 | 3 |
| | 16 | 4 | 2 | 2 | 4 | 4 |
| | 17 | 3 | 3 | 2 | 3 | 4 |
| | 19 | 3 | 1 | 1 | 3 | 4 |
| | 23 | 4 | 0 | 1 | 3 | 4 |
| | 24 | 4 | 2 | 2 | 4 | 4 |
| 3 | 25 | 3 | 0 | 2 | 3 | 4 |
| | 26 | 3 | 0 | 1 | 3 | 4 |
| | 27 | 3 | 0 | 2 | 3 | 4 |
| | 28 | 3 | 3 | 2 | 3 | 4 |
| | 29 | 3 | 0 | 1 | 3 | 4 |
| | 30 | 3 | 1 | 1 | 4 | 4 |
| | 31 | 3 | 0 | 1 | 3 | 3 |
| | 32 | 4 | 0 | 2 | 4 | 4 |
| | 33 | 4 | 0 | 2 | 4 | 4 |
| | 34 | 3 | 1 | 1 | 4 | 3 |
| | 35 | 3 | 1 | 2 | 4 | 4 |
| | 36 | 3 | 0 | 1 | 3 | 4 |

Severity:
0 = Normal;
1 = Minimal;
2 = Mild;
3 = Moderate;
4 = Marked

The skin samples exhibited areas of relatively undamaged skin and areas of damaged skin. The damaged areas in all mice exhibited moderate to marked acanthosis characterized by epidermal thickening due to increased layers of epidermal cells. Frequently, there was minimal to mild parakeratosis accompanying the acanthosis. Foci of epidermal necrosis and/or ulceration were present in the samples from several mice. These foci were characterized by hypereosinphilic, swollen or "ballooned" keratinocytes or focal loss of keratinocytes (ulceration) with necrotic keratinocytes present at the margins of the ulcers. Minimal to mild inflammation characterized by infiltrates of polymorphonuclear and mononuclear inflammatory cells were present in sections from all animals. Moderate to marked adnexal atrophy with follicular necrosis and ectasia was present in all animals. Adnexal atrophy was characterized by decreased numbers or absence of sebaceous glands, decreased numbers of hair follicles, necrosis of sebaceous glands and follicular epithelial cells, and dilation of hair follicles. Moderate to marked dermal/subcutaneous fibrosis was present in sections from all mice. Fibrosis was characterized by thickening of the layer of dermal collagen and an increased density of dermal collagen. As the severity of fibrosis increased, bands of collagen (fibrosis) extended into the hypodermal adipocyte layer.

Findings with similar characteristics were present in all Groups. However, there was a CDC-EV dose related decrease in the severity of acanthosis, inflammation, and adnexal atrophy that was equivocal in the low-dose CDC-EVs Group 2 (0.25 mg/mL), but more clearly evident in the high-dose CDC-EVs Group 3 (1.5 mg/mL). In addition, there was a decrease in both the incidence and severity of epidermal necrosis/ulceration in the high-dose CDC-EVs Group 3 (1.5 mg/mL).

Findings of moderate to marked acanthosis, minimal to mild inflammation, moderate to marked adnexal atrophy/follicular ectasia, and moderate to marked dermal/subcutaneous fibrosis were present in the samples from all mice and many exhibited foci of minimal to moderate epidermal necrosis and/or ulceration. However, there was a CDC-EV dose-related decrease in the severity of acanthosis, inflammation, and adnexal atrophy that was equivocal in the low-dose CDC-EVs Group 2 (0.25 mg/mL), but more clearly evident in the high-dose CDC-EVs Group 3 (1.5 mg/mL). In addition, there was a decrease in both the incidence and severity of epidermal necrosis/ulceration in the high-dose CDC-EVs Group 3 (1.5 mg/mL).

The invention claimed is:

1. A method of preventing or treating cutaneous injury in a subject in need thereof, the method comprising administrating to the subject a therapeutically or prophylactically effective dose of extracellular vesicles, wherein said extracellular vesicles are obtained from cardiospheres or cardiosphere-derived cells (CDCs), or from newt A1 cell line.

2. The method according to claim 1, wherein said cutaneous injury is dermatitis.

3. The method according to claim 2, wherein said dermatitis is radiation-induced dermatitis.

4. The method according to claim 2, wherein said dermatitis is induced by fractionated radiation.

5. The method of claim 3, wherein a therapeutically effective amount of extracellular vesicles is administered one or more times after the subject has received one or more doses of radiation.

6. The method of claim 5, wherein a therapeutically effective amount of extracellular vesicles is administered to a subject 1, 2, 3, 4, 5, 6, 7, and/or 8 weeks after an initial or final radiation exposure, or after the subject has developed generalized erythema caused by radiation, one or more times.

7. The method of claim 6, wherein multiple administrations are made 7 days apart between successive administrations.

8. The method according to claim 1, wherein said extracellular vesicles are exosomes.

9. The method according to claim 8, wherein exosomes are obtained from CDCs using 10 KDa method or 1000 KDa method.

10. The method of claim 1, wherein said administration is via subcutaneous injection, transcutaneous injection, intradermal injection, topical administration, intramuscular injection, injection into lymphoid tissue, injection into the lymphatic system, or systemic administration.

11. A method of preventing or treating radiation-induced dermatitis in a subject who has received radiation therapy, the method comprising administering a therapeutically or prophylactically effective dose of extracellular vesicles following radiation therapy, wherein said extracellular vesicles are obtained from cardiospheres or cardiosphere-derived cells (CDCs), or from newt A1 cell line.

12. The method of claim 11, wherein a therapeutically effective dose of extracellular vesicles is administered following the first clinical manifestation of radiation-induced dermatitis in the subject.

13. The method of claim 12, wherein a prophylactically effective dose of extracellular vesicles is administered following the final radiation therapy treatment.

14. The method according to claim 1, wherein said subject is a human patient.

15. The method of claim 11, wherein a therapeutically effective amount of extracellular vesicles is administered one or more times after the subject has received one or more doses of radiation.

16. The method of claim 15, wherein a therapeutically effective amount of extracellular vesicles is administered to a subject 1, 2, 3, 4, 5, 6, 7, and/or 8 weeks after an initial or final radiation exposure, or after the subject has developed generalized erythema caused by radiation, one or more times.

17. The method of claim 16, wherein multiple administrations are made 7 days apart between successive administrations.

18. The method according to claim 11, wherein said subject is a human patient.

19. The method according to claim 11, wherein said extracellular vesicles are exosomes.

* * * * *